United States Patent
Castellarin et al.

(10) Patent No.: US 12,258,379 B2
(45) Date of Patent: Mar. 25, 2025

(54) COMPOSITIONS AND METHODS FOR SWITCHABLE CAR T CELLS USING SURFACE-BOUND SORTASE TRANSPEPTIDASE

(71) Applicant: THE TRUSTEES OF THE UNIVERSITY OF PENNSYLVANIA, Philadelphia, PA (US)

(72) Inventors: Mauro Castellarin, Ardmore, PA (US); June Carl, Merion Station, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 884 days.

(21) Appl. No.: 17/284,407

(22) PCT Filed: Oct. 12, 2019

(86) PCT No.: PCT/US2019/056011
§ 371 (c)(1),
(2) Date: Apr. 9, 2021

(87) PCT Pub. No.: WO2020/077318
PCT Pub. Date: Apr. 16, 2020

(65) Prior Publication Data
US 2021/0347845 A1    Nov. 11, 2021

Related U.S. Application Data

(60) Provisional application No. 62/745,105, filed on Oct. 12, 2018.

(51) Int. Cl.
| | |
|---|---|
| *C07K 14/705* | (2006.01) |
| *A61K 38/00* | (2006.01) |
| *A61K 39/00* | (2006.01) |
| *A61P 35/00* | (2006.01) |
| *C07K 16/32* | (2006.01) |
| *C12N 9/52* | (2006.01) |

(52) U.S. Cl.
CPC ........ *C07K 14/705* (2013.01); *A61K 39/4611* (2023.05); *A61K 39/4631* (2023.05); *A61K 39/464404* (2023.05); *A61K 39/464406* (2023.05); *A61K 39/464468* (2023.05); *A61P 35/00* (2018.01); *C07K 16/32* (2013.01); *C12N 9/52* (2013.01); *A61K 38/00* (2013.01); *A61K 2239/23* (2023.05); *A61K 2239/31* (2023.05); *C12Y 304/2207* (2013.01)

(58) Field of Classification Search
None
See application file for complete search history.

(56) References Cited

U.S. PATENT DOCUMENTS

| | | | |
|---|---|---|---|
| 11,542,488 B2 * | 1/2023 | Brogdon | ................. C12N 9/52 |
| 2010/0055761 A1 | 3/2010 | Seed | |
| 2017/0137783 A1 | 5/2017 | Bedoya | |
| 2017/0211055 A1 * | 7/2017 | Brogdon | ............... C07K 16/00 |

FOREIGN PATENT DOCUMENTS

| | | |
|---|---|---|
| WO | 2014183066 A2 | 11/2014 |
| WO | 2015/042393 A2 | 3/2015 |
| WO | 2016/014553 A1 | 1/2016 |
| WO | 2017/145427 A1 | 1/2017 |

OTHER PUBLICATIONS

Extended European Search Report issued Jul. 15, 2002 in EP Application No. 19870604.6, 9 pages.
International Search Report and Written Opinion issued Jan. 6, 2020 in International Patent Application No. PCT/US2019/056011.
Marraffini, L. A. et al. "Sortases and the Art of Anchoring Proteins to the Envelopes of Gam-Positive Bacteria", Microbiology and Molecular Biology Reviews, Mar. 2006. vol. 70, No. 1, pp. 199-221, Retrieved from the Internet doi:10.1128/MMBR.70.1>.

* cited by examiner

*Primary Examiner* — Peter J Reddig
(74) *Attorney, Agent, or Firm* — Saul Ewing LLP; Kathryn Doyle

(57) ABSTRACT

The present invention includes compositions and methods comprising sortase immune receptors and sortase chimeric antigen receptors (CARs).

15 Claims, 13 Drawing Sheets

Specification includes a Sequence Listing.

FIG. 7A    SKOV3 killing using Her2-ARM + EGFR-ARM
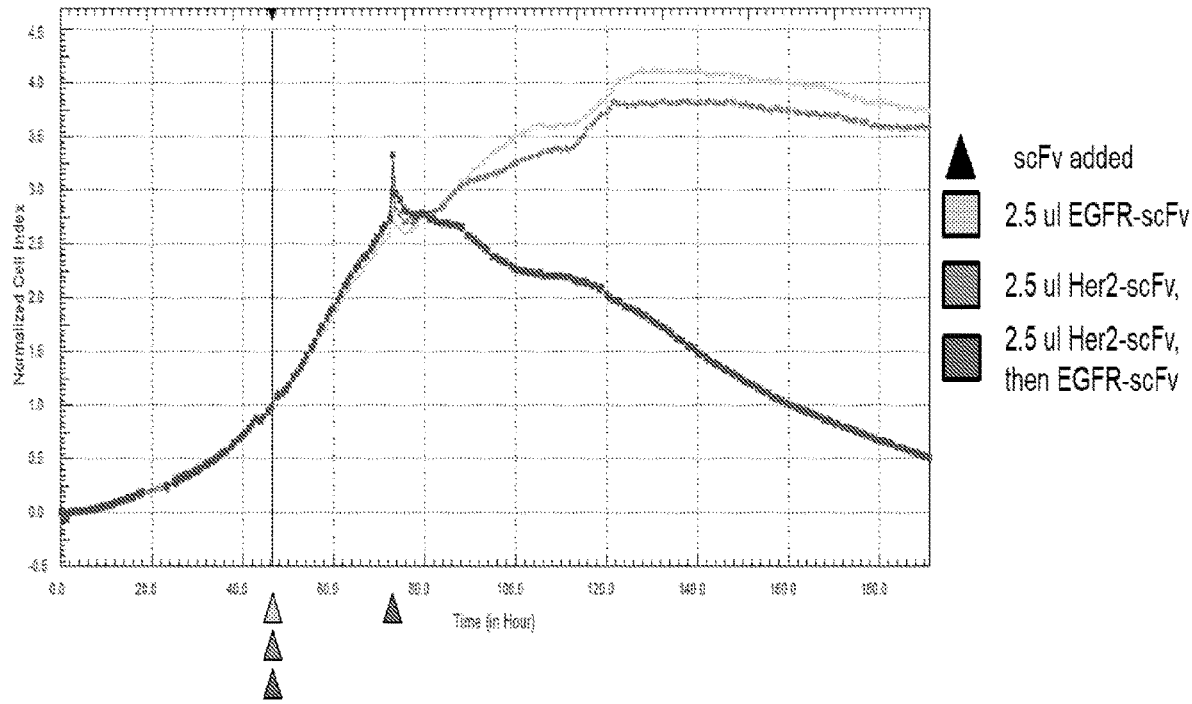
FIG. 7B
CAOV3 killing using MSLN-ARM + EGFR-ARM
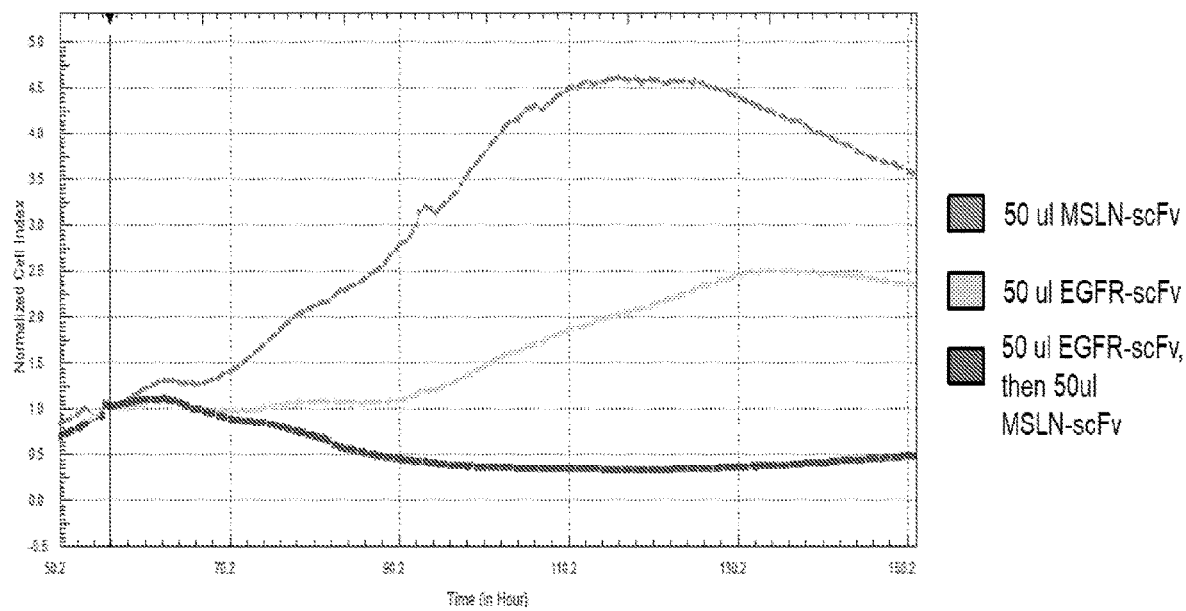

SIR-T gDNA content

IFNγ expression

CD3ε expression

Sortase.bbz Immune Receptor Sequence

Legend:
*Signal sequence*
Sortase
6xHis
*CD8 Hinge*
CD8 transmembrane
4-1BB
CD3zeta

Nucleotide sequence (SEQ ID NO 83):

CTAGCTCTAGAGCCACCATGGCTCTGCCTGTGACAGCTCTGCTGCTGCCTCTGGC
TCTGCTTCTGCATGCCGCTAGACCCATGCAGGCCAAGCCTCAGATCCCCAAGGAC
AAGTCTAAGGTGGCCGGCTACATCGAGATCCCCGACGCCGACATCAAAGAACCTG
TGTACCCTGGACCTGCCACCAGAGAGCAGCTGAATAGAGGCGTGTCCTTCGCCAA
AGAGAACCAGAGCCTGGACGACCAGAACATCTCTATCGCCGGCCACACCTTCATC
GACAGACCCAACTACCAGTTCACCAACCTGAAGGCCGCCAAGAAAGGCAGCATGG
TGTACTTCAAAGTGGGCAACGAGACACGGAAGTACAAGATGACCAGCATCCGGAA
CGTGAAGCCCACCGCTGTGGAAGTGCTGGATGAGCAGAAGGGCAAAGACAAGCA
GCTGACCCTGATCACCTGTGACGACTACAACGAAGAGACAGGCGTGTGGGAGACA
AGAAAGATCTTCGTGGCTACCGAAGTGAAGCTGGAACACCACCACCATCACCACG
gatccaccacgacgccagcgccgcgaccaccaacaccggcgcccaccatcgcgtcgcagccctgtccctg
cgcccagaggcgtgccggccagcggcggggggcgcagtgcacacgagggggctggacttcgcctgtgata
tctacatctggcgccctggccggactgtgtggtccttctcdgtcactggttatcaccctttactgcagcgctaaacggg
gcagaaagaaactcctgtatatattcaaacaaccatttatgagaccagtacaaactactcaagaggaagatgctgtagc
tgccgatttccagaagaagaagaaggaggatgtgaactgagagtgaagttcagcaggagcgcagacgcccccgc
gtacaagcagggccagaaccagctctataacgagctcaatctaggacgaagagaggagtacgatgttttggac
aagagacgtggccgggacccctgagatgggggggaaagccgagaaggaagaaccctcaggaaggcctgtac
aatgaactgcagaaagataagatggcggaggcctacagtgagattgggatgaaaggcgagcgccggaggg
gcaaggggcacgatggcctttaccagggtctcagtacagccaccaaggacacctacgacgcccttcacatgc
aggccctgcccctcgctaa

Amino acid sequence (SEQ ID NO 82):

*MALPVTALLLPLALLLHAARP*MQAKPQIPKDKSKVAGYIEIPDADIKEPVYPGPATREQL
NRGVSFAKENQSLDDQNISIAGHTFIDRPNYQFTNLKAAKKGSMVYFKVGNETRKYKM
TSIRNVKPTAVEVLDEQKGKDKQLTLITCDDYNEETGVWETRKIFVATEVKLEHHHHHH
GS*TTTPAPRPPTPAPTIASQPLSLRPEACRPAAGGAVHTRGLDFACD*YIWAPLAGTC
GVLLLSLVITLYCSAKRGRKKLLYIFKQPFMRPVQTTQEEDGCSCRFPEEEEGGCELRV
KFSRSADAPAYKQGQNQLYNELNLGRREEYDVLDKRRGRDPEMGGKPRRKNPQE
GLYNELQKDKMAEAYSEIGMKGERRRGKGHDGLYQGLSTATKDTYDALHMQALPP
R

FIG. 13

COMPOSITIONS AND METHODS FOR SWITCHABLE CAR T CELLS USING SURFACE-BOUND SORTASE TRANSPEPTIDASE

CROSS-REFERENCE TO RELATED APPLICATION

The present application is a 35 U.S.C. § 371 national phase application from, and claims priority to, International Application No. PCT/US2019/056011, filed Oct. 12, 2019, which is entitled to priority under 35 U.S.C. § 119 (e) to U.S. Provisional Patent Application No. 62/745,105, filed Oct. 12, 2018, which are hereby incorporated by reference in their entireties herein.

REFERENCE TO AN ELECTRONIC SEQUENCE LISTING

The Sequence Listing submitted herewith as an ASCII txt file named "046483-7221US1," created on Oct. 11, 2019 and having a size of 54,654 bytes, is herein incorporated by reference in its entirety.

BACKGROUND OF THE INVENTION

Sortases are a class of transpeptidases found in almost all gram-positive bacteria and they allow pathogens to alter their virulence, infection, and colonization ability by attaching proteins to the cell wall. The sortase enzyme attaches to a "sortase substrate motif", such as Leu-Pro-any-Thr-Gly (LPXTG) (SEQ ID NO: 2), cleaves the peptide between the Thr and Gly, and then covalently attaches this protein to an acceptor peptide, such as polyglycine via a transpeptidation reaction. This process has been utilized by research groups to incorporate site-specific moieties and functional groups on the cell surface of eukaryotic cells in ways that cannot be produced by genetically modifying the cell. Multiple moieties can be attached to a cell surface in predefined proportions based on their stoichiometry.

SUMMARY OF THE INVENTION

As described herein, the present invention relates to compositions and methods comprising sortase immune receptors and sortase chimeric antigen receptors (CARs).

One aspect of the invention includes a sortase immune receptor comprising a sortase enzymatic region, a transmembrane domain, and an intracellular domain.

Another aspect of the invention includes an antigen-binding sortase substrate comprising an antigen-binding domain and a sortase recognition motif.

Yet another aspect of the invention includes a sortase chimeric antigen receptor (CAR) comprising an antigen-binding domain, a sortase recognition motif, a sortase enzymatic region, a transmembrane domain, and an intracellular domain.

Still another aspect of the invention includes a modified T cell comprising a sortase immune receptor. The sortase immune receptor comprises a sortase enzymatic region, a transmembrane domain, and optionally an intracellular domain.

In another aspect, the invention includes a modified T cell comprising a sortase CAR. The sortase CAR comprises an antigen-binding domain, a sortase recognition motif, a sortase enzymatic region, a transmembrane domain, and an intracellular domain.

In yet another aspect, the invention includes a method of producing a sortase chimeric antigen receptor (CAR) T cell. The method comprises providing a T cell with a sortase immune receptor comprising: a sortase enzymatic region, a transmembrane domain, and an intracellular domain. The intracellular domain comprises a costimulatory domain and an intracellular signaling domain. Thereby, an engineered sortase immune receptor T cell is produced. The engineered sortase immune receptor T cell is contacted with a first antigen-binding sortase substrate. The first antigen-binding sortase substrate comprises a first antigen binding domain fused to a first sortase recognition motif. The sortase enzymatic region of the engineered sortase immune receptor T cell recognizes the first sortase recognition motif and mediates an interaction between the first antigen-binding domain and the sortase immune receptor, thereby producing a first sortase CAR T cell.

In still another aspect, the invention includes a method for treating a disease or disorder in a subject in need thereof. The method comprises administering to the subject a therapeutically effective amount of a composition comprising an engineered T cell comprising a sortase CAR. The sortase CAR comprises an antigen-binding domain, a sortase recognition motif, a sortase enzymatic region, a transmembrane domain, and an intracellular domain.

Another aspect of the invention includes a method for treating a disease or disorder in a subject in need thereof comprising administering to the subject a therapeutically effective amount of a composition comprising an engineered T cell comprising a sortase immune receptor and antigen-binding sortase substrate. The sortase immune receptor comprises a sortase enzymatic region, a transmembrane domain, and an intracellular domain. The antigen-binding sortase substrate comprises an antigen-binding domain and a sortase recognition motif.

In various embodiments of the above aspects or any other aspect of the invention delineated herein, the sortase enzymatic region is derived from a sortase or a variant thereof.

In certain embodiments, the sortase is sortase A or a variant thereof. In certain embodiments, the variant thereof is a calcium-independent sortase variant. In certain embodiments, the variant thereof is a truncated sortase. In certain embodiments, the truncated sortase is a truncated sortase A.

In certain embodiments, the intracellular domain comprises a costimulatory domain and an intracellular signaling domain.

In certain embodiments, the interaction between the first antigen-binding domain and the sortase immune receptor is reversible.

In certain embodiments, the first sortase CAR T cell comprises a first sortase CAR comprising the first antigen-binding domain, the first sortase recognition motif, the sortase enzymatic region, the transmembrane domain, and the intracellular domain.

In certain embodiments, the first antigen-binding domain is switchable with a second antigen-binding sortase substrate comprising a second antigen binding domain fused to a second sortase recognition motif.

In certain embodiments, the method further comprises contacting the sortase CAR T cell with the second antigen-binding sortase substrate, wherein the sortase enzymatic region recognizes the second sortase recognition motif and mediates an interaction between the second antigen-binding domain and the sortase immune receptor, thereby producing a second sortase CAR T cell.

In certain embodiments, the second sortase CAR T cell comprises a second sortase CAR comprising the second antigen-binding domain, the second sortase recognition motif, the sortase enzymatic region, the transmembrane domain, and the intracellular domain.

In certain embodiments, the disease is cancer. In certain embodiments, the disease is an autoimmune disease or disorder.

In certain embodiments, the antigen-binding domain comprises a Her2 scFv.

In certain embodiments, the antigen-binding sortase substrate is switchable with a second antigen-binding sortase substrate comprising a second antigen binding domain fused to a second sortase recognition motif.

In certain embodiments, the dosage of the therapeutically effective amount of the antigen-binding sortase substrate is increased or decreased.

In certain embodiments, the method further comprises administering a second sortase CAR, and/or a second sortase immune receptor and/or a second antigen-binding sortase substrate, wherein the antigen binding domain of the CAR and/or the antigen-binding sortase substrate is different from the first CAR and/or the antigen-binding sortase substrate.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 1A illustrates the sortase immune receptor (SIR) comprising an extracellular sortase enzyme (SrtA), a transmembrane domain (TM), and an intracellular signaling domain (ICD) comprising 4-1BB and CD3ζ. The sortase enzyme binds to a sortase recognition motif that can be fused to a variety of molecules to tag them on the cell surface. For example, an scFv that is specifically designed to target a tumor cell antigen (e.g. Her2) can be fused to a sortase substrate, which will bind to the sortase enzyme on the SIR. FIG. 1B is a vector map of the lentiviral construct used to engineer cells to express Srt.bbz.

FIG. 3A is a map of the expression vector used to generate sortase-compatible scFvs. FIG. 3B shows Her2-scFv binding to Her2-positive cells was verified using a Her2$^{LOW}$ cell line, HEK293T, and a Her2$^{HIGH}$ cell line, SKOV3. The Her2-scFv contains a Histidine (His)-tag, which was detected by flow cytometry using anti-His-PE. FIG. 3C shows surface expression of Srt.bbz on Supt1 cells was verified by detection of a His-tag on Srt.bbz. Srt.bbz Supt1 cells were ARMed with Her2-scFv and able to bind Her2-Fc antigen, which was detected with anti-Fc-PE.

FIG. 5A: Sortase-compatible Her2 scFv was administered either daily or "preloaded" on to tumor cells. Daily administration involved adding 1 ul of 14 ng/ul scFv to 200 ul wells for three days and "preloading" tumor cells involved adding 100 ul of 14 ng/ul scFv to the 200 ul well, then incubating for one hour and then washing once prior to adding T cells. FIG. 5B: An effector dosing response was evaluated using a range of effector to target (E:T) ratios. Targets were preloaded as described above. FIG. 5C: An scFv dosing effect on effector function was examined using a serial dilution of preloaded scFv at the concentrations shown.

FIGS. 7A-7B are a set of plots illustrating that the specificity of target cells can be improved using combinations of scFvs.

FIG. 13 illustrates the nucleotide (SEQ ID NO: 83) and amino acid (SEQ ID NO: 82) sequences of the sortase immune receptor.

DETAILED DESCRIPTION

Definitions

Figure 1A:
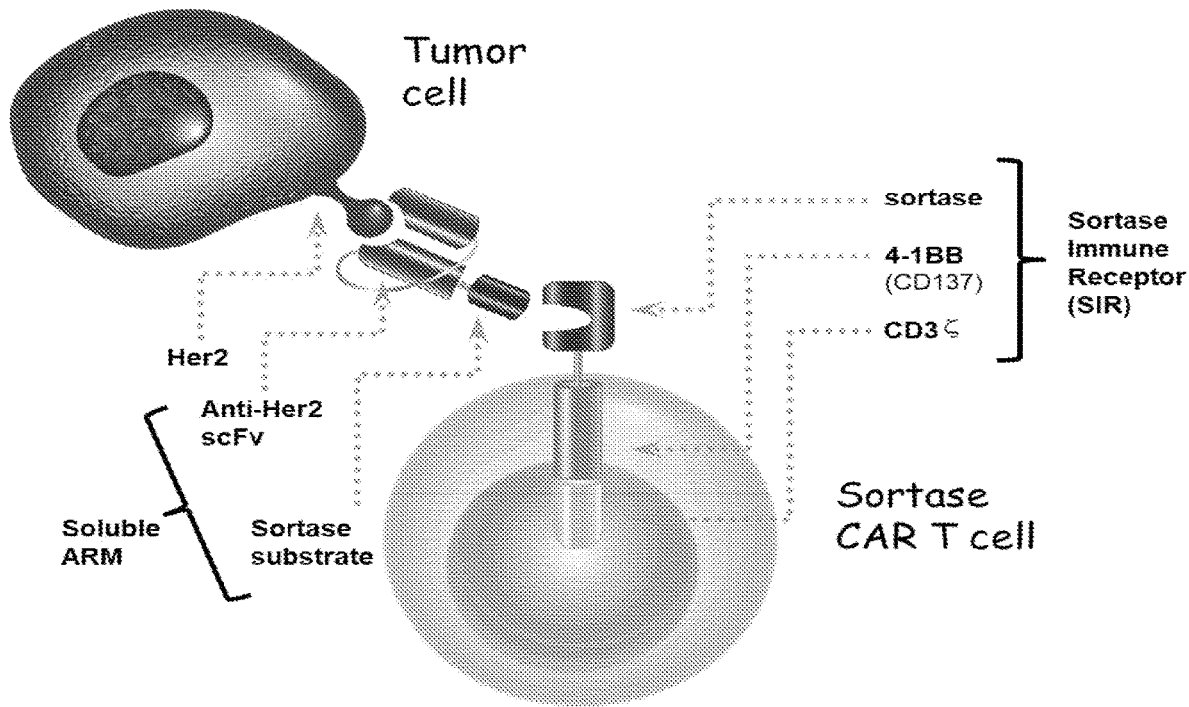
FIGS. 1A-1B are series of diagrams depicting the design of the sortase immune receptor (Srt.bbz).

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. Kappa and lambda light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Allogeneic" refers to any material derived from a different animal of the same species.

"Xenogeneic" refers to any material derived from an animal of a different species.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs has specificity to a selected target, for example a B cell surface receptor. CARs may also comprise an intracellular activation domain, a transmembrane domain and an extracellular domain comprising a tumor associated antigen binding region. In some aspects, CARs comprise an extracellular domain comprising an anti-B cell binding domain fused to CD3-zeta transmembrane and intracellular domain The term "cleavage" refers to the breakage of covalent bonds, such as in the backbone of a nucleic acid molecule or the hydrolysis of peptide bonds. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522-525, 1986; Reichmann et al., Nature, 332:323-329, 1988; Presta, Curr. Op. Struct. Biol., 2:593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

When "an immunologically effective amount," "an autoimmune disease-inhibiting effective amount," or "therapeutic amount" is indicated, the precise amount of the compositions of the present invention to be administered can be determined by a physician or researcher with consideration of individual differences in age, weight, tumor size, extent of infection or metastasis, and condition of the patient (subject).

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "Sendai virus" refers to a genus of the Paramyxoviridae family. Sendai viruses are negative, single stranded RNA viruses that do not integrate into the host genome or alter the genetic information of the host cell. Sendai viruses have an exceptionally broad host range and are not pathogenic to humans Used as a recombinant viral vector, Sendai viruses are capable of transient but strong gene expression.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

The term "sortase substrate motif" is used interchangeably herein with "sortase substrate ligand" and "sortase recognition motif" and refers to a polypeptide which, upon cleavage by a sortase molecule, forms a thioester bond with the sortase molecule. In one embodiment, the sortase recognition motif comprises LPXTG. In certain embodiments, the sortase recognition motif comprises a sequence from any of Tables 1-6. In an embodiment, sortase cleavage occurs between T and G/A. In an embodiment the peptide bond between T and G/A is replaced with an ester bond to the sortase molecule.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides, in one aspect, a sortase immune receptor comprising a sortase enzymatic region, a transmembrane domain, and an intracellular domain. The invention also provides an antigen-binding sortase substrate comprising an antigen binding domain and a sortase recognition motif. In another aspect, the invention provides a sortase chimeric antigen receptor (CAR) comprising an antigen-binding domain, a sortase recognition motif, a sortase enzymatic region, a transmembrane domain, and an intracellular domain.

Sortases

The sortases are a family of enzymes that, in nature, play a role in the formation of the bacterial cell wall by covalently linking specific surface proteins to a peptidoglycan. The sortase enzyme recognizes a sortase recognition motif (e.g. LPXTG) (SEQ ID NO: 2) in a substrate protein and carries out a transpeptidation reaction. In the first step of the reaction, the sortase cleaves a peptide bond in the sortase recognition motif, forming an acyl intermediate with the cleaved sortase recognition motif. In the second step, the sortase binds to an acceptor protein or precursor cell wall component bearing a sortase acceptor motif and transfers the acyl intermediate to this N-terminus. The end result is formation of a new peptide bond between the C-terminus of the protein and the N-terminus of the acceptor protein or precursor of the cell wall component.

Sortase transpeptidation, also known as "sortase labeling" or "sortagging," can be used for bioconjugation of two proteins.

Sortases have been classified into 4 classes by sequence alignment and phylogenetic analysis of sortases from gram-positive bacterial genomes: Sortase A, Sortase B, Sortase C, and Sortase D (Dramsi, et al., *Res Microbial.*, 156 (3): 289-97, 2005). Each class also comprises subfamilies, as follows: Sortase A (Subfamily 1), Sortase B (Subfamily 2), Sortase C (Subfamily 3), Sortase D (Subfamily 4 and Subfamily 5) (Comfort and Clubb, *Infect Immun.*, 72 (5): 2710-22, 2004). Two additional classes, Sortase E and Sortase F, were recently identified by sequence analysis (Spirig et al., *Mal Microbial.*, 2011). The skilled artisan would readily be able to assign an identified sortase to the correct class and/or subfamily based on its sequence or functional characteristics (e.g., transpeptidation activity).

Compositions and methods disclosed herein can use or include a sortase from any bacterial species or strain, e.g., a Sortase A, a Sortase B, a Sortase C, a Sortase D, a Sortase E, a Sortase F, or a sortase from a yet unidentified class of sortase enzymes. All gram-positive bacteria examined to date possess at least one major housekeeping sortase (e.g., Sortase A) (Barnett et al., *J Bacteriology* 2004). The methods described herein can be used to evaluate candidate sortases.

The amino acid sequences of many sortases and the nucleotide sequences that encode them are known to those of skill in the art and are disclosed in the references cited herein. The amino acid sequence of full-length, wild-type *S. aureus* Sortase A is as follows:

```
                                         (SEQ ID NO: 1)
MKKWTNRLMTIAGVVLILVAAYLFAKPHIDNYLHDKDKDEKIEQYDKNV

KEQASKDNKQQAKPQIPKDKSKVAGYIEIPDADIKEPVYPGPATPEQLN

RGVSFAEENESLDDQNISIAGHTFIDRPNYQFTNLKAAKKGSMVYFKVG

NETRKYKMTSIRDVKPTDVEVLDEQKGKDKQLTLITCDDYNEKTGVWEK

RKIFVATEVK
```

Other sortases with transamidase activity can be identified by sequence comparison and analysis. Newly identified sortases are also contemplated in the methods described herein. For example, a transamidase with 10%, 20%, 30%, 40%, or 50% or more sequence identity with an *S. pyogenes*, *S. aureus*, *A. neslundii*, *S. mutans*, *E. faecalis*, or *B. subtilis* open reading frame encoding a sortase can be used in the methods described herein. Sortases identified and displaying comparable transamidase activity to that of sortase A or sortase B from *S. aureus* can be utilized. As used herein, comparable transamidase activity refers to at least 10%, at least 15%, at least 20%, at least 25%, at least 30%, at least 40%, or at least 50% activity with respect to the activity of *S. aureus* sortase A.

The sortase enzymatic region in the immune receptor or CAR of the present invention can be derived from any sortase, or any sortase variant, or any sortase mutant. In one embodiment, the sortase is Sortase A or a variant thereof. Sortase variants include but are not limited to calcium-independent sortase variants and truncated sortases (e.g. truncated sortase A). An exemplary sortase mutant, is *S. aureus* Sortase A mutant [P94R/E105K/E108Q/D160N/D165A/K190E/K196T]. It lacks the N-terminal 59 amino acids of *S. aureus* Sortase A and includes mutations that render the enzyme calcium independent and makes the enzyme faster. (The number of residues herein begin with the first residue at the N terminal end of nontruncated *S. aureus* Sortase A.). The primary amino acid sequence is provided below. Mutations are in bold. The underlined residue is E in this embodiment but can be any amino acid, e.g., a conservative substitution. The primary amino acid sequence of Sortase A mutant [P94R/E105K/E108Q/D160N/D165A/K190E/K196T] is as follows:

```
                                         (SEQ ID NO: 62)
MQAKPQIPKD KSKVAGYIEI PDADIKEPVY PGPATREQLN

RGVSFAKENQ SLDDQNISIA GHTFIDRPNY QFTNLKAAKK

GSMVYFKVGN ETRKYKMTSI RNVKPTAVEV LDEQKGKDKQ

LTLITCDDYN EETGVWETRK IFVATEVKLE HHHHHH
```

Sortase Recognition Motif

Certain aspects of the invention provide an antigen-binding sortase substrate and/or a sortase CAR comprising a sortase recognition motif. "Sortase substrate motif" is used interchangeably herein with "sortase substrate ligand" and "sortase recognition motif." In the first step of a sortase-mediated transamidation reaction, the sortase recognizes a substrate with a sortase recognition motif. When the sortase enzyme attaches to a sortase substrate motif, such as Leu-Pro-any-Thr-Gly (LPXTG) (SEQ ID NO: 2), it cleaves the peptide between the Thr and Gly, and then covalently attaches this protein to an acceptor peptide, such as polyglycines via a transpeptidation reaction. Any and all sortase recognition motifs disclosed herein can be included in the CARs or antigen-binding substrates disclosed herein.

In certain embodiments, the sortase recognition motif is LPXTG, where X is any amino acid (SEQ ID NO: 2). In certain embodiments, the sortase recognition motif is LPETG (SEQ ID NO: 3). In certain embodiments, the sortase recognition motif is LPXTX, where X is any amino acid (SEQ ID NO: 4).

A sortase from one class (A, B, C, D) may recognize a sortase recognition motif that is different from another sortase class. Alternatively, a sortase from one class may recognize the same sortase recognition motif as another sortase class. A first moiety to be coupled to a second moiety can first be coupled to a sortase recognition motif. A sortase can then be used to couple the first moiety to a second moiety coupled to a sortase acceptor motif.

In certain embodiments, the Sortase A recognition motif can have the following structure:

$$X_4\text{-}X_3\text{-}X_2\text{-}X_1\text{-}|\text{-}X_0$$

Wherein (SEQ ID NO: 5):
$X_4$ = L or I
$X_3$ = P or G
$X_2$ = X
$X_1$ = T or A
$X_0$ = X,
and wherein X is any amino acid.

In certain embodiments, the sortase recognition motif is selected from any of the Sortase A recognition motifs included in Table 1, any of the Sortase B recognition motifs included in Table 2, any of the Sortase C recognition motifs included in Table 3, any of the Sortase D recognition motifs included in Table 4, any of the other Sortase recognition motifs included in Table 5, or any of the general Sortase recognition motifs included in Table 6.

TABLE 1

Sortase A Recognition Motifs

| Sortase A Recognition Motif Structure | wherein | SEQ ID NO: |
|---|---|---|
| $X_4\text{-}X_3\text{-}X_2\text{-}X_1\text{-}|\text{-}X_0$ | $X_4$ = L or I; $X_3$ = P or G; $X_2$ = X; $X_1$ = T or A; $X_0$ = X; and X is any amino acid. | 5 |
| | $X_4$ = L; $X_3$ = P; $X_2$ = X; $X_1$ = T; $X_0$ = X and X is any amino acid. | 4 |
| | $X_4$ = L or I; $X_3$ = P or G; $X_2$ = K, A, N, E, or Q; $X_1$ = T or A; and $X_0$ = A or G. | 6 |
| | $X_4$ = L; $X_3$ = P; $X_2$ = K, A, N, E, or Q; $X_1$ = T; $X_0$ = X; and X is any amino acid. | 7 |
| | $X_4$ = L; $X_3$ = P; $X_2$ = K, A, N, E, or Q; $X_1$ = T; and $X_0$ = G. | 8 |
| | $X_4$ = L; $X_3$ = P; $X_2$ = K; $X_1$ = T; and $X_0$ = G. | 9 |
| | $X_4$ = L; $X_3$ = P; $X_2$ = A; $X_1$ = T; and $X_0$ = G. | 10 |
| | $X_4$ = L; $X_3$ = P; $X_2$ = N; $X_1$ = T; and $X_0$ = G. | 11 |
| | $X_4$ = L; $X_3$ = P; $X_2$ = E; $X_1$ = T; and $X_0$ = G. | 12 |
| | $X_4$ = L; $X_3$ = P; $X_2$ = X; $X_1$ = A; $X_0$ = G; and X is any amino acid. | 13 |
| | $X_4$ = L; $X_3$ = P; $X_2$ = N; $X_1$ = A; and $X_0$ = G. | 14 |
| | $X_4$ = L; $X_3$ = P; $X_2$ = X; $X_1$ = T; $X_0$ = A; and X is any amino acid. | 15 |
| | $X_4$ = L; $X_3$ = P; $X_2$ = N; $X_1$ = T; and $X_0$ = A. | 16 |
| | $X_4$ = L; $X_3$ = G; $X_2$ = X; $X_1$ = T; $X_0$ = G; and X is any amino acid. | 17 |
| | $X_4$ = L; $X_3$ = G; $X_2$ = A; $X_1$ = T; and $X_0$ = G | 18 |
| | $X_4$ = I; $X_3$ = P; $X_2$ = X; $X_1$ = T; $X_0$ = G; and X is any amino acid. | 19 |
| | $X_4$ = I; $X_3$ = P; $X_2$ = N; $X_1$ = T; and $X_0$ = G. | 20 |
| | $X_4$ = I; $X_3$ = P; $X_2$ = E; $X_1$ = T; and $X_0$ = G. | 21 |

TABLE 2

Sortase B Recognition Motifs

| Sortase B Recognition Motif Structure | wherein | SEQ ID NO: |
|---|---|---|
| $X_4\text{-}X_3\text{-}X_2\text{-}X_1\text{-}|\text{-}X_0$ | $X_4$ = N; $X_3$ = P, A or S; $X_2$ = X; $X_1$ = T or S; $X_0$ = X; and X is any amino acid. | 22 |
| | $X_4$ = N; $X_3$ = P, S or A; $X_2$ = Q or K; $X_1$ = T or S; and $X_0$ = A, H, N, G, or S. | 23 |
| | $X_4$ = N; $X_3$ = P; $X_2$ = X; $X_1$ = T; $X_0$ = X, and X is any amino acid. | 24 |
| | $X_4$ = N; $X_3$ = P; $X_2$ = Q or K; $X_1$ = T; and $X_0$ = H, N, G, or S. | 25 |
| | $X_4$ = N; $X_3$ = P; $X_2$ = Q; $X_1$ = T; and $X_0$ = N. | 26 |
| | $X_4$ = N; $X_3$ = P; $X_2$ = K; $X_1$ = T; and $X_0$ = G. | 27 |
| | $X_4$ = N; $X_3$ = S; $X_2$ = K; $X_1$ = T; and $X_0$ = A. | 28 |
| | $X_4$ = N; $X_3$ = P; $X_2$ = Q; $X_1$ = T; and $X_0$ = G. | 29 |
| | $X_4$ = N; $X_3$ = A; $X_2$ = K; $X_1$ = T; and $X_0$ = N. | 30 |
| | $X_4$ = N; $X_3$ = P; $X_2$ = Q; $X_1$ = S; and $X_0$ = S. | 31 |

TABLE 3

Sortase C Recognition Motifs

| Sortase C Recognition Motif Structure | wherein | SEQ ID NO: |
|---|---|---|
| $X_4\text{-}X_3\text{-}X_2\text{-}X_1\text{-}|\text{-}X_0$ | $X_4$ = L; $X_3$ = P; $X_2$ = X; $X_1$ = T; $X_0$ = X; and X is any amino acid. | 32 |
| | $X_4$ = L; $X_3$ = P; $X_2$ = K, S, E, L, A or N; $X_1$ = T; and $X_0$ = G. | 33 |

TABLE 4

Sortase D Recognition Motifs

| Sortase D Recognition Motif Structure | wherein | SEQ ID NO: |
|---|---|---|
| $X_4$--$X_3$--$X_2$--$X_1$-\|-$X_0$ | $X_4$ = L or N; $X_3$ = P or A; $X_2$ = X; $X_1$ = T; $X_0$ = G or A; and X is any amino acid. | 101 |
| | $X_4$ = N; $X_3$ = A; $X_2$ = E, A, S, or H; $X_1$ = T; and $X_0$ = G. | 102 |
| | $X_4$ = L; $X_3$ = P; $X_2$ = X; $X_1$ = T; $X_0$ = A; and X is any amino acid. | 15 |
| | $X_4$ = L; $X_3$ = P; $X_2$ = N; $X_1$ = T; and $X_0$ = A. | 16 |
| | $X_4$ = L; $X_3$ = A; $X_2$ = X; $X_1$ = T; $X_0$ = G; and X is any amino acid. | 34 |

TABLE 5

Other Sortase Recognition Motifs

| Other Sortase Recognition Motif Structure | wherein | SEQ ID NO: |
|---|---|---|
| $X_4$--$X_3$--$X_2$--$X_1$-\|-$X_0$ | $X_4$ = L; $X_3$ = P; $X_2$ = I; $X_1$ = T; and $X_0$ = G. | 35 |
| | $X_4$ = L; $X_3$ = P; $X_2$ = D; $X_1$ = T; and $X_0$ = A. | 36 |
| | $X_4$ = L; $X_3$ = P; $X_2$ = L; $X_1$ = T; and $X_0$ = G. | 37 |
| | $X_4$ = L; $X_3$ = P; $X_2$ = M; $X_1$ = T; and $X_0$ = G. | 38 |
| | $X_4$ = L; $X_3$ = P; $X_2$ = O; $X_1$ = T; and $X_0$ = S. | 39 |
| | $X_4$ = L; $X_3$ = A; $X_2$ = X; $X_1$ = T; $X_0$ = X; and X is any amino acid. | 40 |
| | $X_4$ = L; $X_3$ = A; $X_2$ = E; $X_1$ = T; and $X_0$ = G. | 41 |
| | $X_4$ = L; $X_3$ = A; $X_2$ = A; $X_1$ = T; and $X_0$ = G. | 42 |
| | $X_4$ = L; $X_3$ = A; $X_2$ = H; $X_1$ = T; and $X_0$ = G. | 43 |
| | $X_4$ = L; $X_3$ = A; $X_2$ = S; $X_1$ = T; and $X_0$ = G. | 44 |
| | $X_4$ = L; $X_3$ = A; $X_2$ = F; $X_1$ = T; and $X_0$ = G. | 45 |
| | $X_4$ = L; $X_3$ = P; $X_2$ = X; $X_1$ = A; $X_0$ = X; and X is any amino acid. | 46 |
| | $X_4$ = L; $X_3$ = A; $X_2$ = X; $X_1$ = T; $X_0$ = X; and X is any amino acid. | 47 |
| | $X_4$ = L; $X_3$ = G; $X_2$ = X; $X_1$ = T; $X_0$ = X; and X is any amino acid. | 48 |
| | $X_4$ = I; $X_3$ = P; $X_2$ = X; $X_1$ = T; $X_0$ = X; and X is any amino acid. | 49 |
| | $X_4$ = I; $X_3$ = P; $X_2$ = Q; $X_1$ = T; and $X_0$ = G. | 50 |
| | $X_4$ = N; $X_3$ = P; $X_2$ = X; $X_1$ = T; $X_0$ = X; and X is any amino acid. | 51 |
| | $X_4$ = N; $X_3$ = P; $X_2$ = Q; $X_1$ = S; $X_0$ = X; and X is any amino acid. | 52 |
| | $X_4$ = N; $X_3$ = S; $X_2$ = K; $X_1$ = T; $X_0$ = X; and X is any amino acid. | 53 |
| | $X_4$ = N; $X_3$ = P; $X_2$ = Q; $X_1$ = T; $X_0$ = X; and X is any amino acid. | 54 |
| | $X_4$ = N; $X_3$ = A; $X_2$ = K; $X_1$ = T; $X_0$ = X; and X is any amino acid. | 55 |
| | $X_4$ = L; $X_3$ = S; $X_2$ = R; $X_1$ = T; and $X_0$ = G. | 56 |
| | $X_4$ = S; $X_3$ = P; $X_2$ = K; $X_1$ = T; and $X_0$ = G. | 57 |
| | $X_4$ = V; $X_3$ = P; $X_2$ = D; $X_1$ = T; and $X_0$ = G. | 58 |
| | $X_4$ = Y; $X_3$ = P; $X_2$ = R; $X_1$ = R; and $X_0$ = G. | 59 |
| | $X_4$ = Q; $X_3$ = V; $X_2$ = P; $X_1$ = T; and $X_0$ = G. | 60 |

TABLE 6

General Sortase Recognition Motifs

| General Sortase Recognition Motif Structure | wherein | SEQ ID NO: |
|---|---|---|
| $X_4$--$X_3$--$X_2$--$X_1$-\|-$X_0$ | $X_4$ = L, N, I, Y, Q, V, or S; $X_3$ = P, G, A, S, or V; $X_2$ = Xa; $X_1$ = T, A, S, or R; $X_0$ = $X_b$; and wherein $X_a$ and $X_b$ can be any amino acid. In some embodiments, $X_a$ and $X_b$ are different amino acids. In some embodiments, $X_a$ and $X_b$ are the same amino acid. | 61 |

Transmembrane Domain

The invention provides a sortase immune receptor and/or a sortase CAR comprising a transmembrane domain. The transmembrane domain can connect the sortase enzymatic region to the intracellular domain of the sortase immune receptor or sortase CAR. In one embodiment, the transmembrane domain is naturally associated with one or more of the domains in the CAR or immune receptor. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR or immune receptor into a cell membrane, e.g., an artificial hydrophobic sequence. Examples of the transmembrane regions of particular use in this invention include, without limitation, transmembrane domains derived from (i.e. comprise at least the transmembrane region(s) of) the alpha, beta or zeta chain of the T-cell receptor, CD28, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), Toll-like receptor 1 (TLR1), TLR2, TLR3, TLR4, TLR5, TLR6, TLR7, TLR8, and TLR9. In some instances, a variety of hinges can be employed as well including the Ig (immunoglobulin) hinge. In one embodiment, the sortase CAR comprises a CD8 transmembrane domain. In one embodiment, the sortase immune receptor comprises a CD8 transmembrane domain.

In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

The transmembrane domains described herein can be combined with any of the intracellular domains described herein, or any of the other domains described herein that may be included in the sortase CAR or sortase immune receptor.

In some embodiments, the transmembrane domain further comprises a hinge region. The CAR or immune receptor of the present invention may also include an hinge region. The hinge region of the CAR or immune receptor is a hydrophilic region which is located between the sortase enzymatic region and the transmembrane domain. In some embodiments, this domain facilitates proper protein folding for the CAR. The hinge region is an optional component for the CAR or immune receptor. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4). In some embodiments, the hinge region is an immunoglobulin heavy chain hinge region. In some embodiments, the hinge region is a hinge region polypeptide derived from a receptor (e.g., a CD8-derived hinge region).

The hinge region can have a length of from about 4 amino acids (aa) to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

For example, hinge regions include glycine polymers $(G)_n$, glycine-serine polymers (including, for example, $(GS)_n$, $(GSGGS)_n$ (SEQ ID NO: 95) and $(GGGS)_n$ (SEQ ID NO: 63), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, *Rev. Computational. Chem.* (1992) 2:73-142). Exemplary hinge regions can comprise amino acid sequences including, but not limited to, GGSG (SEQ ID NO: 64), GGSGG (SEQ ID NO: 65), GSGSG (SEQ ID NO: 66), GSGGG (SEQ ID NO: 67), GGGSG (SEQ ID NO: 68), GSSSG (SEQ ID NO: 69), and the like.

In some embodiments, the hinge region is an immunoglobulin heavy chain hinge region. Immunoglobulin hinge region amino acid sequences are known in the art; see, e.g., Tan et al., *Proc. Natl. Acad. Sci. USA* (1990) 87 (1): 162-166; and Huck et al., *Nucleic Acids Res.* (1986) 14 (4): 1779-1789. As non-limiting examples, an immunoglobulin hinge region can include one of the following amino acid sequences: DKTHT (SEQ ID NO: 70); CPPC (SEQ ID NO: 71); CPEPKSCDTPPPCPR (SEQ ID NO: 72) (see, e.g., Glaser et al., *J. Biol. Chem.* (2005) 280:41494-41503); ELKTPLGDTTHT (SEQ ID NO: 73); KSCDKTHTCP (SEQ ID NO: 74); KCCVDCP (SEQ ID NO: 75); KYGPPCP (SEQ ID NO: 76); EPKSCDKTHTCPPCP (SEQ ID NO: 77) (human IgG1 hinge); ERKCCVECPPCP (SEQ ID NO: 78) (human IgG2 hinge); ELKTPLGDTTHTCPRCP (SEQ ID NO: 79) (human IgG3 hinge); SPNMVPHAHHAQ (SEQ ID NO: 80) (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO: 81) see, e.g., Yan et al., J. Biol. Chem. (2012) 287:5891-5897. In one embodiment, the hinge region can comprise an amino acid sequence derived from human CD8, or a variant thereof.

In one embodiment, the transmembrane domain comprises a CD8 transmembrane domain. In another embodiment, the transmembrane domain comprises a CD8 hinge domain and a CD8 transmembrane domain. The transmembrane domain may be combined with any hinge domain and/or may comprise one or more transmembrane domains described herein.

Intracellular Domain (ICD)

The present invention provides a sortase immune receptor and/or a sortase CAR comprising an intracellular domain. The intracellular domain is responsible for activation of at least one of the effector functions of the cell in which the CAR or immune receptor is expressed (e.g., immune cell). The intracellular domain transduces the effector function signal and directs the cell (e.g., immune cell) to perform its specialized function, e.g., harming and/or destroying a target cell. In certain embodiments, the intracellular domain comprises a costimulatory domain and an intracellular signaling domain. In one embodiment, the intracellular domain comprises 4-1BB and CD3 zeta.

Examples of intracellular domains for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular signaling domain include, without limitation, the ζ chain of the T cell receptor complex or any of its homologs, e.g., η chain, FcsRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcγRIII, FcsRI, cytoplasmic tails of Fc receptors, an immunoreceptor tyrosine-based activation motif (ITAM) bearing cytoplasmic receptors, and combinations thereof.

In one embodiment, the intracellular domain includes any portion of one or more co-stimulatory molecules, such as at least one signaling domain from CD3, CD8, CD27, CD28, ICOS, 4-IBB, PD-1, any derivative or variant thereof, any synthetic sequence thereof that has the same functional capability, and any combination thereof.

Other examples of the intracellular domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon Rib), CD79a, CD79b, Fcgamma Rlla, DAP10, DAP 12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD 160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 Id, ITGAE, CD 103, ITGAL, CD 11 a, LFA-1, ITGAM, CD lib, ITGAX, CD 11c, ITGBI, CD29, ITGB2, CD 18, LFA-1, ITGB7, TNFR2, TRANCE/ RANKL, DNAMl (CD226), SLAMF4 (CD244, 2B4), CD84, CD 96 (Tactile), CEACAMI, CRT AM, Ly9 (CD229), CD160 (BY55), PSGLI, CD100 (SEMA4D), CD69, SLAMF6 (NTB-A, Ly108), SLAM (SLAMF1, CD150, IPO-3), BLAME (SLAMF8), SELPLG (CD 162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33 (6): 651-653). Additionally, intracellular signaling domains may include signaling domains used by NK and NKT cells (see, e.g., Hermanson and Kaufman, Front. Immunol. (2015) 6:195) such as signaling domains of NKp30 (B7-H6) (see, e.g., Zhang et al., J. Immunol. (2012) 189 (5): 2290-2299), and DAP 12 (see, e.g., Topfer et al., J. Immunol. (2015) 194 (7): 3201-3212), NKG2D, NKp44, NKp46, DAP10, and CD3z.

Intracellular signaling domains suitable for use in the present invention include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR or immune receptor (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound CAR or immune receptor, but is instead diffused in the cytoplasm.

Intracellular signaling domains suitable for use in a subject CAR or immune receptor of the present invention include immunoreceptor tyrosine-based activation motif (ITAM)-containing intracellular signaling polypeptides. In some embodiments, an ITAM motif is repeated twice in an intracellular signaling domain, where the first and second instances of the ITAM motif are separated from one another by 6 to 8 amino acids. In one embodiment, the intracellular signaling domain of a subject CAR comprises 3 ITAM motifs. In some embodiments, intracellular signaling domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., Front. Immunol. (2014) 5:254).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular signaling domain is derived from FCER1G (also known as FCRG; Fc epsilon receptor I gamma chain; Fc receptor gamma-chain; fc-epsilon RI-gamma; fcRgamma; fceRI gamma; high affinity immunoglobulin epsilon receptor subunit gamma; immunoglobulin E receptor, high affinity, gamma chain; etc.). In one embodiment, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular signaling domain suitable for use in the CAR or immune receptor of the present disclosure includes a DAP10/CD28 type signaling chain. In one embodiment, an intracellular signaling domain suitable for use in the CAR or immune receptor of the present disclosure includes a ZAP70 polypeptide. In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular signaling domain in the CAR or immune receptor includes a cytoplasmic signaling domain of human CD3 zeta.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

The intracellular signaling domains described herein can be combined with any of any of the transmembrane domains described herein, or any of the other domains described herein that may be included in the CAR or immune receptor.

Sortase Immune Receptor

The invention provides a sortase immune receptor comprising a sortase enzymatic region, a transmembrane domain, and an intracellular domain. The invention also provides an engineered T cell comprising the sortase immune receptor. The sortase immune receptor can comprise any sortase enzymatic region, any transmembrane domain, and any intracellular domain disclosed herein. In one embodiment, the sortase enzymatic region is derived from a sortase. In one embodiment, the sortase enzymatic region is derived from a sortase variant. In one embodiment, the sortase enzymatic region is derived from a sortase A. In one embodiment, the sortase enzymatic region is derived from a sortase A variant. In one embodiment, the sortase enzymatic region is derived from a calcium-independent sortase variant. In one embodiment, the sortase enzymatic region is derived from a truncated sortase. In one embodiment, the sortase enzymatic region is derived from a truncated sortase A. In one embodiment, the sortase enzymatic region comprises the amino acid sequence of SEQ ID NO: 62. In one embodiment, the intracellular domain of the immune receptor comprises a costimulatory domain and an intracellular signaling domain. In one embodiment, the sortase immune receptor comprises a CD8 hinge region, a CD8 transmembrane region, a 4-1BB motif and a CD3z motif. In one embodiment, the sortase immune receptor comprises a truncated Sortase A region, a CD8 hinge region, a CD8 transmembrane region, a 4-1BB motif and a CD3z motif. In one embodiment, the CD8 hinge region comprises the amino acid sequence of SEQ ID NO: 111. In one embodiment, the CD8 hinge region is encoded by the nucleotide sequence of SEQ ID NO: 105. In one embodiment, the CD8 transmembrane region comprises the amino acid sequence of SEQ ID NO: 112. In one embodiment, the CD8 transmembrane region is encoded by the nucleotide sequence of SEQ ID NO: 106. In one embodiment, the 4-1BB motif comprises the amino acid sequence of SEQ ID NO: 113. In one embodiment, the 4-1BB motif is encoded by the nucleotide sequence of SEQ ID NO: 107. In one embodiment, the CD3 zeta motif comprises the amino acid sequence of SEQ ID NO: 114. In one embodiment, the CD3 zeta motif is encoded by the nucleotide sequence of SEQ ID NO: 108. In one embodiment, the sortase immune receptor comprises the amino acid sequence of SEQ ID NO: 82. In one embodiment, the sortase immune receptor is encoded by the nucleotide sequence of SEQ ID NO: 83.

The sortase immune receptor can be coupled with any antigen-binding sortase substrate.

Antigen-Binding Sortase Substrate

In one aspect, the invention provides an antigen-binding sortase substrate comprising an antigen-binding domain and a sortase recognition motif. The antigen-binding sortase substrate can comprise any antigen-binding domain disclosed herein and/or any sortase recognition motif disclosed herein.

Antigen Binding Domain

The antigen binding domain can include any domain that binds to an antigen and may include, but is not limited to, a monoclonal antibody, a polyclonal antibody, a synthetic antibody, a human antibody, a humanized antibody, a non-human antibody, and any fragment thereof, including an antigen binding fragment (Fab), and a single-chain variable fragment (scFv). In certain embodiments, the antigen binding domain is referred to as an antigen recognition molecule (ARM). In a preferred embodiment, the antigen binding domain is a single-chain variable fragment (scFV).

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen binding domain (e.g., TAA binding domain) comprises an scFv having the configuration from N-terminus to C-terminus, VH-linker-VL. In some embodiments, the antigen binding domain comprises an scFv having the configuration from N-terminus to C-terminus, VL-linker-VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80 (6): 1910-1917 (2008) and WO 2014/087010, the contents of which are hereby incorporated by reference in their entireties. Various linker sequences are known in the art, including, without limitation, glycine serine (GS) linkers such as $(GS)_n$, $(GSGGS)_n$ (SEQ ID NO:84), $(GGGS)_n$ (SEQ ID NO: 85), and $(GGGGS)_n$ (SEQ ID NO:86), where n represents an integer of at least 1. Exemplary linker sequences can comprise amino acid sequences including, without limitation, GGSG (SEQ ID NO:87), GGSGG (SEQ ID NO:88), GSGSG (SEQ ID NO: 89), GSGGG (SEQ ID NO:90), GGGSG (SEQ ID NO:91), GSSSG (SEQ ID NO:92), GGGGS (SEQ ID NO:93), GGGGSGGGGSGGGGS (SEQ ID NO:94) and the like. Those of skill in the art would be able to select the appropriate linker sequence for use in the present invention. In one embodiment, an antigen binding domain of the present invention comprises a heavy chain variable region (VH) and a light chain variable region (VL), wherein the VH and VL is separated by the linker sequence having the amino acid sequence GGGGSGGGGSGGGGS (SEQ ID NO:94), which may be encoded by the nucleic acid sequence ggtggcggtggctcgggcggtggtgggtcgggtggcggcggatct (SEQ ID NO: 96).

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27 (6): 455-51; Peter et al., J Cachexia Sarcopenia Muscle 2012-8-12; Shieh et al., J Imunol 2009 183 (4): 2277-85; Giomarelli et al., Thromb Haemost 2007 97 (6): 955-63; Fife eta., J Clin Invst 2006 116 (8): 2252-61; Brocks et al., Immunotechnology 1997 3 (3): 173-84; Moosmayer et al., Ther Immunol 1995 2 (10:31-40). Agonistic scFvs having stimulatory activity have been described (see, e.g., Peter et al., J Bioi Chem 2003 25278 (38): 36740-7; Xie et al., Nat Biotech 1997 15 (8): 768-71; Ledbetter et al., Crit Rev Immunol 1997 17 (5-6): 427-55; Ho et al., BioChim Biophys Acta 2003 1638 (3): 257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some instances, the antigen binding domain may be derived from the same species in which the CAR or immune receptor will ultimately be used. For example, for use in humans, the antigen binding domain may comprise a human antibody as described elsewhere herein, or a fragment thereof. In one embodiment, the antigen binding domain portion comprises a mammalian antibody or a fragment thereof.

The antigen binding domain may be operably linked to the sortase recognition motif, described elsewhere herein, for expression in the cell. In one embodiment, a nucleic acid encoding the antigen binding domain is operably linked to a nucleic acid encoding the sortase recognition motif.

The antigen binding domain of the CAR or immune receptor is an extracellular region that binds to a specific target antigen including proteins, carbohydrates, and glycolipids. In some embodiments, the CAR or immune receptor comprises affinity to a target antigen on a target cell. The target antigen may include any type of protein, or epitope thereof, associated with the target cell. For example, the CAR or immune receptor may comprise affinity to a target antigen on a target cell that indicates a particular disease state of the target cell.

As described herein, a CAR or immune receptor of the present disclosure having affinity for a specific target antigen on a target cell may comprise a target-specific binding domain. In some embodiments, the target-specific binding domain is a murine target-specific binding domain, e.g., the target-specific binding domain is of murine origin. In some embodiments, the target-specific binding domain is a human target-specific binding domain, e.g., the target-specific binding domain is of human origin.

In some embodiments, the CAR or immune receptor of the present disclosure may have affinity for one or more target antigens on one or more target cells. In such embodiments, the CAR is a bispecific CAR, or a multispecific CAR. In such embodiments, the immune receptor is a bispecific immune receptor, or a multispecific immune receptor. In some embodiments, the CAR or immune receptor comprises one or more target-specific binding domains that confer affinity for one or more target antigens. In some embodiments, the CAR or immune receptor comprises one or more target-specific binding domains that confer affinity for the same target antigen. For example, a CAR or immune receptor comprising one or more target-specific binding domains having affinity for the same target antigen could bind distinct epitopes of the target antigen. When a plurality of target-specific binding domains is present in a CAR or immune receptor, the binding domains may be arranged in tandem and may be separated by linker peptides. For example, in a CAR or immune receptor comprising two target-specific binding domains, the binding domains are connected to each other covalently on a single polypeptide chain, through an oligo- or polypeptide linker, an Fc hinge region, or a membrane hinge region.

In one embodiment, the antigen binding domain binds to a tumor antigen, such as an antigen that is specific for a tumor or cancer of interest. In one embodiment, the tumor antigen of the present invention comprises one or more antigenic cancer epitopes. In one embodiment, the antigen binding domain is a Her2-scFv. In one embodiment, the Her2-scFv comprises SEQ ID NO: 98. In one embodiment, the Her2-scFv is encoded by the nucleotide sequence of SEQ ID NO: 97.

```
Her2-scFv nucleotide sequence (SEQ ID NO: 97):
ATGGATTTTCAGGTGCAGATTTTCAGCTTCCTGCTAATCAGTGCCTCAG

TCATAATGTCCAGAGGAGATATCCAGATGACCCAGTCCCCGAGCTCCCT

GTCCGCCTCTGTGGGCGATAGGGTCACCATCACCTGCCGTGCCAGTCAG

GATGTGAATACTGCTGTAGCCTGGTATCAACAGAAACCAGGAAAAGCTC

CGAAACTACTGATTTACTCGGCATCCTTCCTTTATTCTGGAGTCCCTTC

TCGCTTCTCTGGATCTAGATCTGGGACGGATTTCACTCTGACCATCAGC

AGTCTGCAGCCGGAAGACTTCGCAACTTATTACTGTCAGCAACATTATA

CTACTCCTCCCACGTTCGGACAGGGTACCAAGGTGGAGATCAAACGCAC

TGGGTCTACATCTGGATCTGGGAAGCCGGGTTCTGGTGAGGGTTCTGAG

GTTCAGCTGGTGGAGTCTGGCGGTGGCCTGGTGCAGCCAGGGGGCTCAC

TCCGTTTGTCCTGTGCAGCTTCTGGCTTCAACATTAAAGACACCTATAT

ACACTGGGTGCGTCAGGCCCCGGGTAAGGGCCTGGAATGGGTTGCAAGG

ATTTATCCTACGAATGGTTATACTAGATATGCCGATAGCGTCAAGGGCC

GTTTCACTATAAGCGCAGACACATCCAAAAACACAGCCTACCTGCAGAT

GAACAGCCTGCGTGCTGAGGACACTGCCGTCTATTATTGTTCTAGATGG

GGAGGGGACGGCTTCTATGCTATGGACGTGTGGGGTCAAGGAACCCTGG

TCACCGTCTCCTCG

Her2-scFv protein sequence (SEQ ID NO: 98):
MDFQVQIF SFLLISASVIMSRGDIQMTQSPSSLSASVGDRVTITCRAS

QDVNTAVAWYQQKPGKAPKLLIYSASFLYSGVPSRFSGSRSGTDFTLTI

SSLQPEDFATYYCQQHYTTPPTFGQGTKVEIKRTGSTSGSGKPGSGEGS

EVQLVESGGGLVQPGGSLRLSCAASGFNIKDTYIHWVRQAPGKGLEWVA

RTYPTNGYTRYADSVKGRFTISADTSKNTAYLQMNSLRAEDTAVYYCSR

WGGDGFYAMDVWGQGTLVTVSS
```

Chimeric Antigen Receptor (CAR)

The present invention provides herein a sortase chimeric antigen receptor (CAR) comprising an antigen-binding domain, a sortase recognition motif, a sortase enzymatic region, a transmembrane domain, and an intracellular domain. The invention also provides a sortase chimeric antigen receptor (CAR) T cell comprising a sortase CAR comprising an antigen-binding domain, a sortase recognition motif, a sortase enzymatic region, a transmembrane domain, and an intracellular domain.

The sortase CAR can comprise any antigen-binding domain, any sortase recognition motif, any sortase enzymatic region, any transmembrane domain, and any intracellular domain, as disclosed in detail elsewhere herein. In one embodiment, the sortase CAR comprises an antigen binding domain comprising Her2-scFv. In one embodiment, the sortase CAR comprises a sortase recognition motif comprising LPETG (SEQ ID NO: 3). In one embodiment, the sortase CAR comprises a CD8 hinge region. In one embodiment, the sortase CAR comprises a CD8 transmembrane region. In one embodiment, the sortase CAR comprises, a 4-1BB motif and/or a CD3z motif.

In one embodiment, the sortase CAR comprises an antigen binding domain comprising Her2-scFv, a sortase recognition motif comprising LPETG (SEQ ID NO: 3), a CD8 hinge region, a CD8 transmembrane region, and an intracellular signaling domain comprising a 4-1BB motif and a CD3z motif. In one embodiment, the sortase CAR comprises the amino acid sequence of SEQ ID NO: 100. In one embodiment, the sortase CAR is encoded by the nucleotide sequence of SEQ ID NO: 99.

```
Sortase CAR nucleotide sequence (SEQ ID NO: 99):
ATGGCTCTGCCTGTGACAGCTCTGCTGCTGCCTCTGGCTCTGCTTCTGC

ATGCCGCTAGACCCATGCAGGCCAAGCCTCAGATCCCCAAGGACAAGTC

TAAGGTGGCCGGCTACATCGAGATCCCCGACGCCGACATCAAAGAACCT

GTGTACCCTGGACCTGCCACCAGAGAGCAGCTGAATAGAGGCGTGTCCT

TCGCCAAAGAGAACCAGAGCCTGGACGACCAGAACATCTCTATCGCCGG

CCACACCTTCATCGACAGACCCAACTACCAGTTCACCAACCTGAAGGCC

GCCAAGAAAGGCAGCATGGTGTACTTCAAAGTGGGCAACGAGACACGGA

AGTACAAGATGACCAGCATCCGGAACGTGAAGCCCACCGCTGTGGAAGT

GCTGGATGAGCAGAAGGGCAAAGACAAGCAGCTGACCCTGATCACCTGT

GACGACTACAACGAAGAGACAGGCGTGTGGGAGACAAGAAAGATCTTCG

TGGCTACCGAAGTGAAGCTGGAACACCACCACCATCACCACGGATCCAC

CACGACGCCAGCGCCGCGACCACCAACACCGGCGCCCACCATCGCGTCG

CAGCCCCTGTCCCTGCGCCCAGAGGCGTGCCGGCCAGCGGCGGGGGCG

CAGTGCACACGAGGGGCTGGACTTCGCCTGTGATATCTACATCTGGGC

GCCCTTGGCCGGGACTTGTGGGGTCCTTCTCCTGTCACTGGTTATCACC

CTTTACTGCAGCGCTAAACGGGGCAGAAAGAAACTCCTGTATATATTCA

AACAACCATTTATGAGACCAGTACAAACTACTCAAGAGGAAGATGGCTG

TAGCTGCCGATTTCCAGAAGAAGAAGAAGGAGGATGTGAACTGAGAGTG

AAGTTCAGCAGGAGCGCAGACGCCCCCGCGTACAAGCAGGGCCAGAACC

AGCTCTATAACGAGCTCAATCTAGGACGAAGAGAGGAGTACGATGTTTT

GGACAAGAGACGTGGCCGGGACCCTGAGATGGGGGGAAAGCCGAGAAGG

AAGAACCCTCAGGAAGGCCTGTACAATGAACTGCAGAAAGATAAGATGG

CGGAGGCCTACAGTGAGATTGGGATGAAAGGCGAGCGCCGGAGGGGCAA

GGGGCACGATGGCCTTTACCAGGGTCTCAGTACAGCCACCAAGGACACC

TACGACGCCCTTCACATGCAGGCCCTGCCCCCTCGC

Sortase CAR protein sequence (SEQ ID NO: 100):
MALPVTALLLPLALLLHAARPMQAKPQIPKDKSKVAGYIEIPDADIKEP

VYPGPATREQLNRGVSFAKENQSLDDQNISIAGHTFIDRPNYQFTNLKA
```

```
-continued
AKKGSMVYFKVGNETRKYKMTSIRNVKPTAVEVLDEQKGKDKQLTLITC

DDYNEETGVWETRKIFVATEVKLEHHHHHHGSTTTPAPRPPTPAPTIAS

QPLSLRPEACRPAAGGAVHTRGLDFACDIYIWAPLAGTCGVLLLSLVIT

LYCSAKRGRKKLLYIFKQPFMRPVQTTQEEDGCSCRFPEEEEGGCELRV

KFSRSADAPAYKQGQNQLYNELNLGRREEYDVLDKRRGRDPEMGGKPRR

KNPQEGLYNELQKDKMAEAYSEIGMKGERRRGKGHDGLYQGLSTATKDT

YDALHMQALPPR
```

Methods

Another aspect of the invention includes a method of producing a sortase chimeric antigen receptor (CAR) T cell. The method comprises providing a T cell with a sortase immune receptor. The sortase immune receptor comprises a sortase enzymatic region, a transmembrane domain, and an intracellular domain, wherein the intracellular domain comprises a costimulatory domain and an intracellular signaling domain. Thereby, an engineered sortase immune receptor T cell is produced. The engineered sortase immune receptor T cell is contacted with a first antigen-binding sortase substrate. The first antigen-binding sortase substrate comprises a first antigen binding domain fused to a first sortase recognition motif. The sortase enzymatic region of the engineered sortase immune receptor T cell recognizes the first sortase recognition motif and mediates an interaction between the first antigen-binding domain and the sortase immune receptor, thereby producing a first sortase CAR T cell.

In certain embodiments, the interaction between the first antigen-binding domain and the sortase immune receptor is reversible.

In certain embodiments, the first sortase CAR T cell comprises a first sortase CAR comprising the first antigen-binding domain, the first sortase recognition motif, the sortase enzymatic region, the transmembrane domain, and the intracellular domain. In certain embodiments, the first antigen-binding domain is switchable with a second antigen-binding sortase substrate comprising a second antigen binding domain fused to a second sortase recognition motif.

In certain embodiments, the method further comprises contacting the sortase CAR T cell with the second antigen-binding sortase substrate, wherein the sortase enzymatic region recognizes the second sortase recognition motif and mediates an interaction between the second antigen-binding domain and the sortase immune receptor, thereby producing a second sortase CAR T cell. In certain embodiments, the second sortase CAR T cell comprises a second sortase CAR comprising the second antigen-binding domain, the second sortase recognition motif, the sortase enzymatic region, the transmembrane domain, and the intracellular domain.

Methods of Treatment

The present invention includes methods for treating a disease or disorder. In one embodiment, the disease is cancer. In another embodiment, the disease is an autoimmune disease. In one aspect, the method comprises administering to a subject in need thereof a therapeutically effective amount of a composition comprising an engineered T cell comprising a sortase CAR. In another aspect, the method comprises administering to a subject in need thereof a therapeutically effective amount of a composition comprising an engineered T cell comprising a sortase immune receptor and antigen-binding sortase substrate. The sortase CAR or sortase immune receptor comprise an antigen binding domain that targets an antigen specific for the disease or disorder to be treated. In one embodiment, the sortase CAR or sortase immune receptor comprise a Her2-specific antigen binding domain (e.g. Her2 scFv), which targets and binds a cancer/tumor cell.

In certain embodiments, a sortase CAR Treg is used to promote immune suppression for the treatment of autoimmune disease.

The initiation and cessation of the treatment method comprising a sortase immune receptor and antigen-binding sortase substrate can be controlled via dosing or withdrawal of the antigen-binding sortase substrate. For example, increased dosages of the antigen-binding sortase substrate can be administered as needed to amplify the treatment regimen. Alternatively, the antigen binding sortase substrate can be withdrawn to cease the treatment. Concentrations and dosages to be administered can be determined by one of skill in the art.

Multiple antigen-binding sortase substrates can be designed and used to target different tumor clonal populations. For example, different tumor cells can be targeted by using different sortase-compatible scFvs that recognize different tumor antigens.

Introduction of Nucleic Acids

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12 (8): 861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5:505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Moreover, the nucleic acids may be introduced by any means, such as transducing the expanded T cells, transfecting the expanded T cells, and electroporating the expanded T cells. One nucleic acid may be introduced by one method and another nucleic acid may be introduced into the T cell by a different method.

RNA

In one embodiment, the nucleic acids introduced into the T cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric membrane protein. By way of example, the template encodes an antibody, a fragment of an antibody or a portion of an antibody. By way of another example, the template comprises an extracellular domain comprising a single chain variable domain of an antibody, such as anti-CD3, and an intracellular domain of a co-stimulatory molecule. In one embodiment, the template for the RNA chimeric membrane protein encodes a chimeric membrane protein comprising an extracellular domain comprising an antigen binding domain derived from an antibody to a co-stimulatory molecule, and an intracellular domain derived from a portion of an intracellular domain of CD28 and 4-1BB.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The poly A/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli poly A polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES)

sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA is electroporated into the cells, such as in vitro transcribed RNA.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

The invention provides engineered T cells comprising a sortase immune receptor and/or a sortase CAR.

In certain embodiments, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

Any type of T cell or T cell line may be used in the invention, including but not limited to Th1, Th2, CD4+, CD8+, CTL, Treg, Supt1, and NF-kB/Jurkat/GFP reporter cells. In one embodiment, the T cell is a primary cell.

Expansion of T Cells

In certain embodiments, the T cells can be expanded by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

Pharmaceutical Compositions

Pharmaceutical compositions of the present invention may comprise the modified T cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The cells of the invention to be administered may be autologous, allogeneic or xenogeneic with respect to the subject undergoing therapy.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It can generally be stated that a pharmaceutical composition comprising the modified T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the modified T cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction:

Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

Figure 1B:
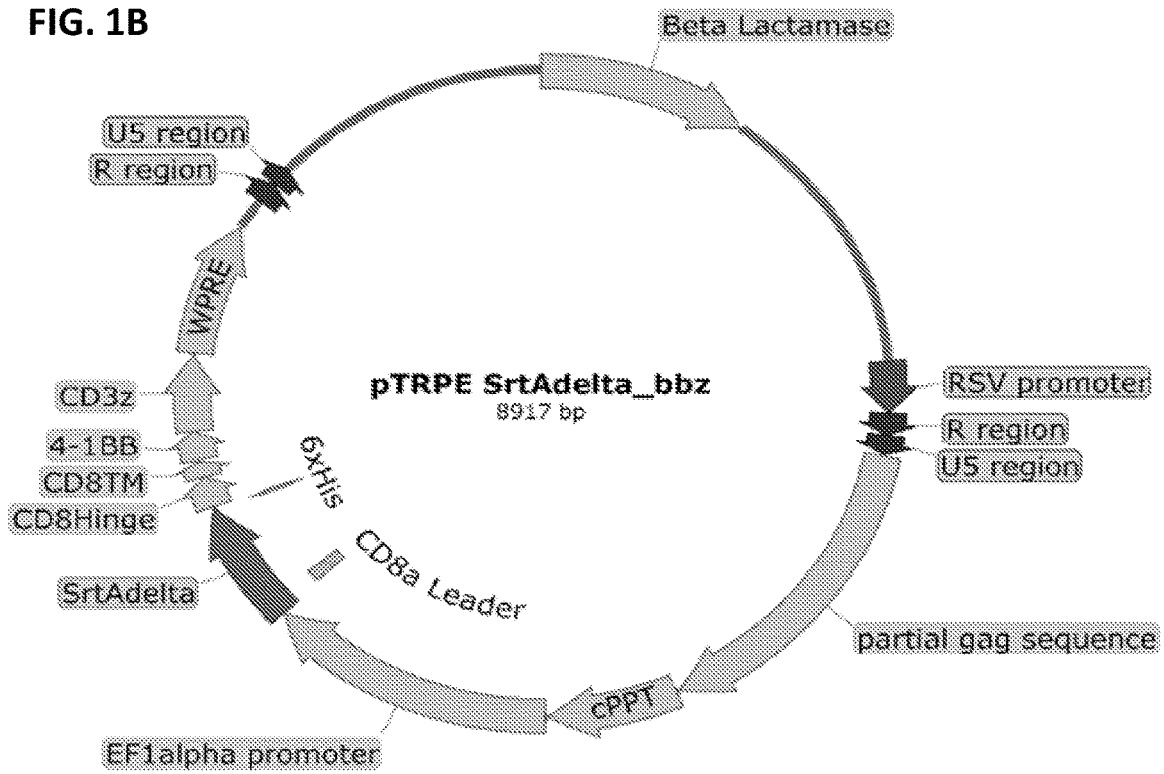
Figure 3A:
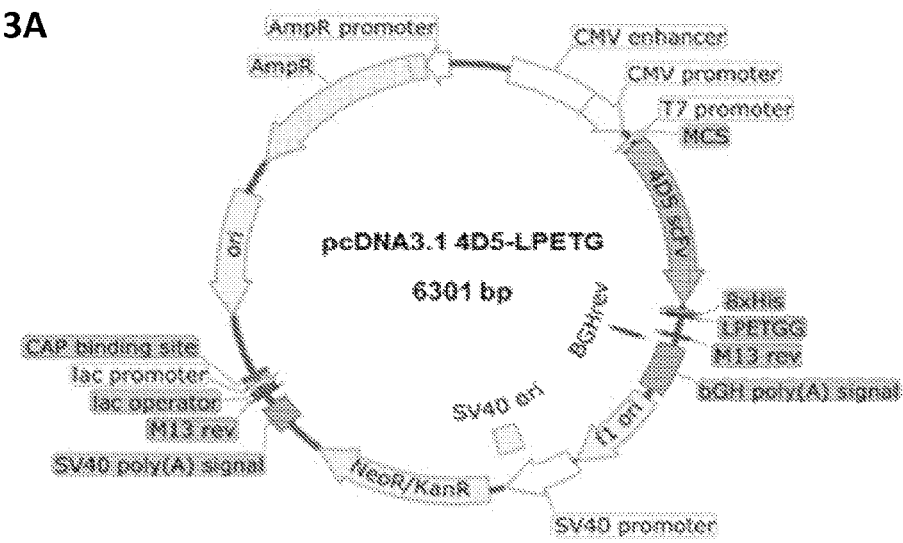
FIGS. 3A-3C are series of graphs illustrating tagging Srt.bbz cells with sortase-compatible antigen recognition molecules (ARMs).

Lentivirus was made using a lentiviral vector that encoded a truncated version of the sortase enzyme fused to a CD8 hinge region, a CD8 transmembrane region, a 4-1BB motif and a CD3z motif (FIG. 1B). Either Supt1 cells, NF-kB/Jurkat/GFP reporter cells, or primary T cells were genetically modified using the Srt.bbz lentivirus to express the Srt.bbz receptor. The Srt.bbz Supt1 cells were used first to optimize conditions for tagging cells with either the reporter probes or ARMs. T cell activation via the NF-kB signaling pathway was monitored in the Srt.bbz Jurkat reporter cells by detecting GFP expression. Cytolytic activity of tumor cells by primary Srt.bbz T cells was performed using an Xcelligence cell killing assay. Single variable fragments (scFvs) were used as the ARMs, which were custom synthesized to contain the sortase substrate ligand, LPETG (SEQ ID NO: 3), on their carboxy terminal end. Protein production was performed by constructing expression vectors that encoded a Her2-scFv fused to a histidine (His)-tag and the LPETG (SEQ ID NO: 3) peptide (FIG. 3A). The DNA vector was then transfected into HEK293T cells and the culture supernatant that contained the secreted Her2-scFv was collected.

The results of the experiments are now described.

Example 1: Results

Figure 2:
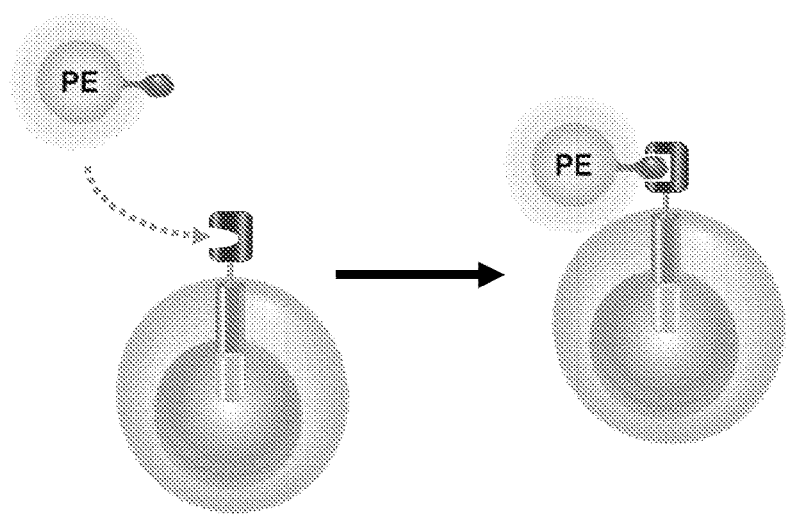
FIG. 2 is a graph illustrating sortase-tagging the cell surface of living cells. Supt1 cells were engineered to express the Srt.bbz receptor and incubated with serial dilutions of a sortase-compatible probe that contained the phycoerythrin (PE) fluorophore. Adhesion of the probe on the cell surface was detected by flow cytometry and is shown by the histogram of PE fluorescence. PE fluorescence was used to calculate the percentage of cells that contained probe on their surface and the mean fluorescent intensity (MFI) correlates to the number of probes on the cell surface.
Figure 2:
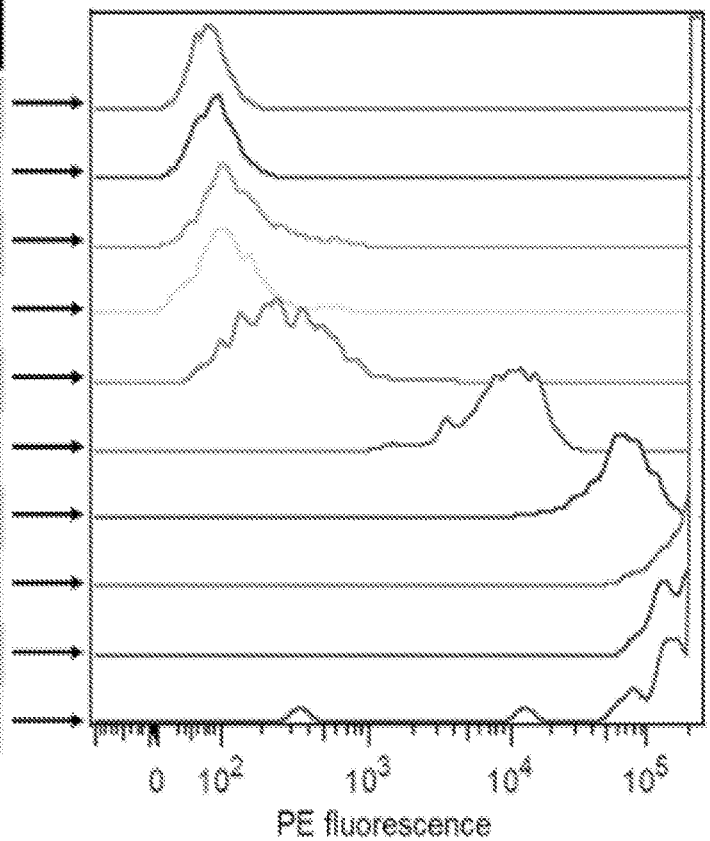

Supt1 cells were engineered to express a surface-bound Sortase receptor ("Srt.bbz") (FIG. 1A). The Srt.bbz Supt1 cells were tested for their ability to recognize and bind a reporter probe consisting of a sortase-recognition motif and the fluorophore, phycoerythrin (PE). The PE-probe was serially diluted 10-fold and added to Srt.bbz Supt1 cells, and then PE-positive Supt1 cells were detected using flow cytometry. PE-probes were successfully tagged in 100% of the Srt.bbz Supt1 cells at probe concentrations ranging from 250 uM to 25 nM and PE-probe tagging was detected on some of the cells when the probe concentration were in the picomolar range (FIG. 2). An increase in probe concentration also resulted in a greater number of probes attached per cell, as indicated by an increase in mean fluorescent intensity. No PE-probe was tagged in the untransduced (UTD) Supt1s even at the highest probe concentrations.

Figure 3B:
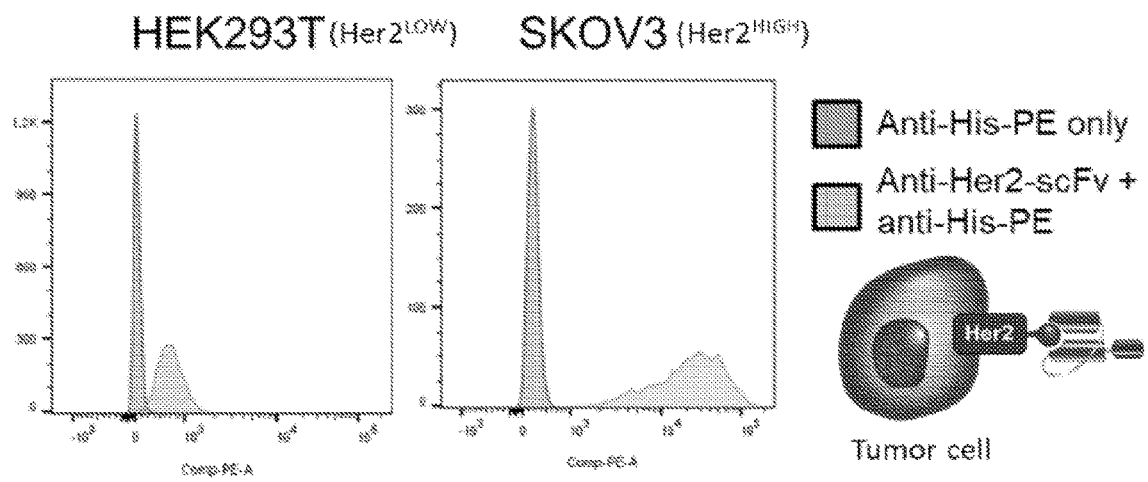
Figure 3C:
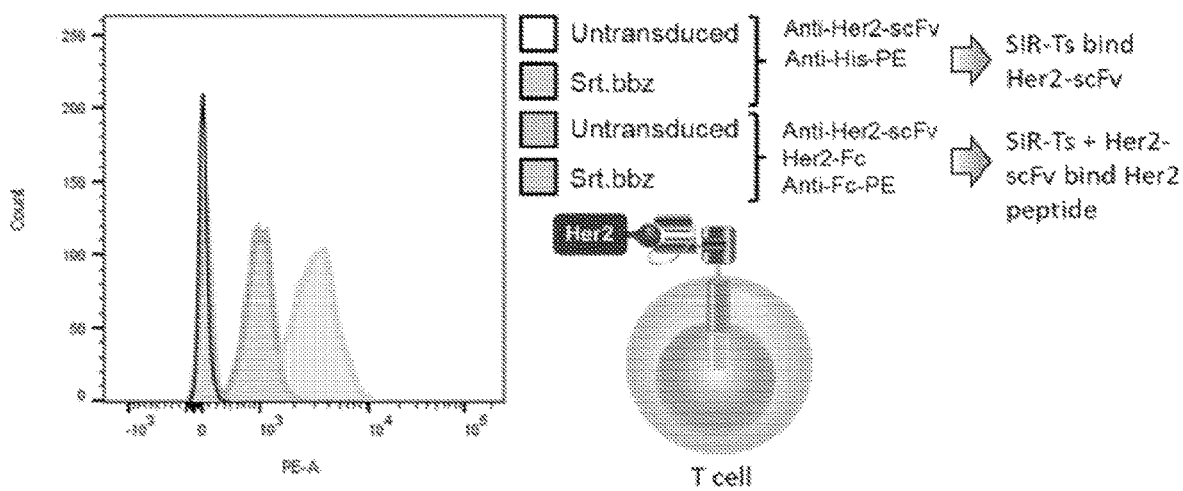

Next, Srt.bbz Supt1 cells were tested for their ability to bind sortase-compatible ARMs ("ARMed T cells") using Her2-scFv as the recognition molecule. First, custom Her2-scFvs were produced and tested for cognate antigen recognition on the Her2-positive cancer cell lines, SKOV3 and HEK293T cells (FIG. 3B). Next, the Her2-scFvs were tested to see whether they bind Srt.bbz receptor by adding the Her2-scFv to Srt.bbz Supt1 cells and then surface-bound scFv was detected by their His-tag (FIG. 3C). Furthermore, to show that the ARMs can confer antigen recognition to the Srt.bbz Supt1 cells, the cells were ARMed with Her2-scFv and then incubated with recombinant Her2-Fc antigen. Her2-Fc bound to the ARMed Supt1 cells was detected by flow cytometry using anti-Fc-PE (FIG. 3C).

Figure 4:
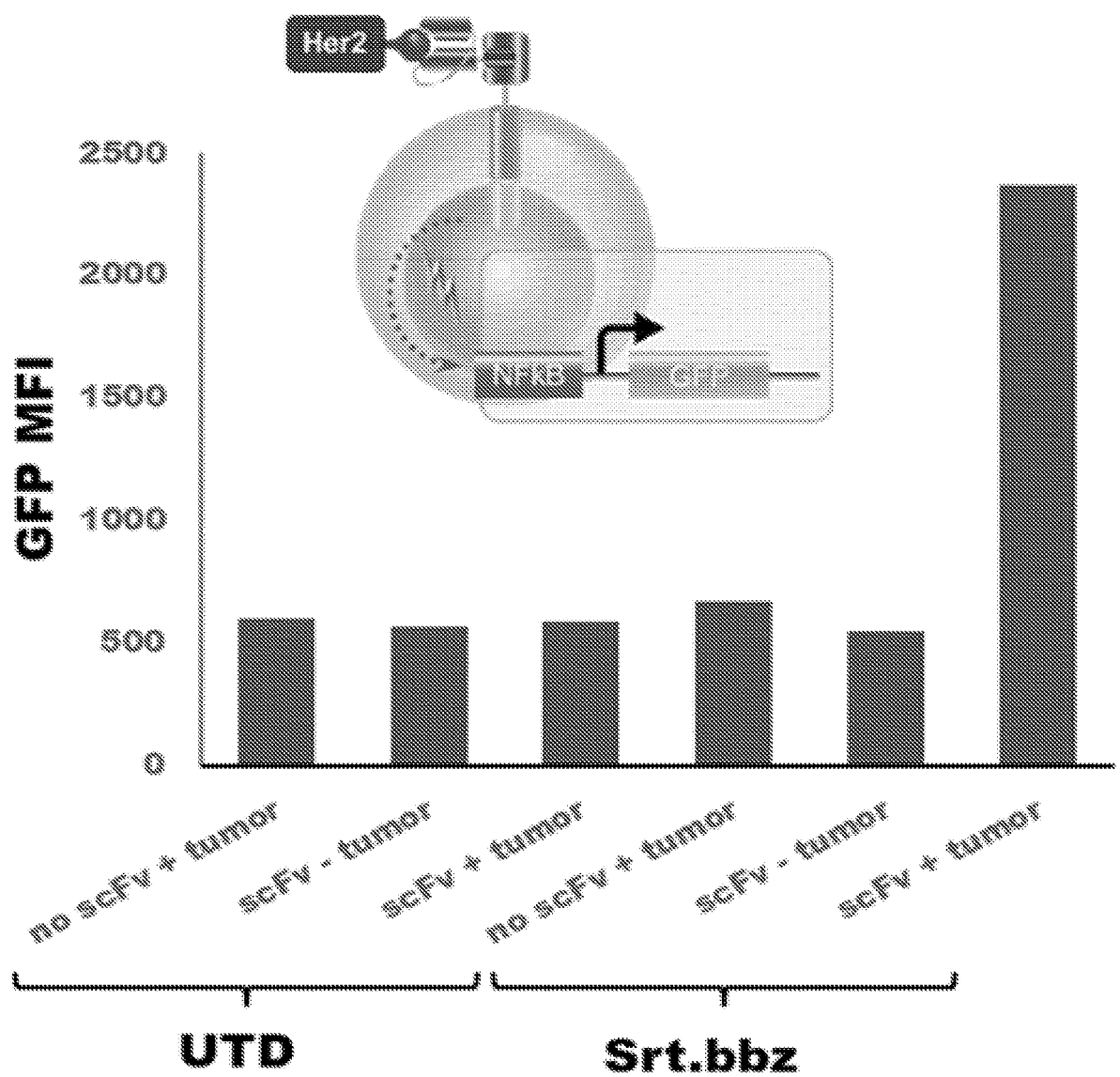
FIG. 4 is a graph illustrating T-cell receptor signaling via Srt.bbz. Antigen stimulation of TCR signaling can be monitored using Jurkat-NFkB-GFP reporter cells by their expression of GFP. These Jurkat cells were transduced with lentiviral Srt.bbz receptor and then ARMed with Her2-scFvs in the presence of the Her2-positive tumor cell line, SKOV3. Negative controls included unARMed Srt.bbz Jurkat reporter cells with tumor cells, ARMed Srt.bbz Jurkat reporter cells without tumor cells, and untransduced Jurkat reporter cells with Her2-scFv and with tumor. GFP fluorescence was detected by flow cytometry.

NF-kB/Jurkat/GFP reporter cells were used to detect TCR signal transduction through the Srt.bbz receptor. These Jurkat cells were engineered to express the Srt.bbz receptor, then they were ARMed with Her2-scFvs and exposed to Her2 antigen on the SKOV3 tumor cell line. ARMed Srt.bbz Jurkat cells in the presence of the Her2-positive tumor cells had higher levels of GFP expression than either unARMed Srt.bbz Jurkat cells with antigen or ARMed Srt.bbz Jurkats without antigen (FIG. 4). Negative control Jurkat cells that did not express the Srt.bbz receptor had low levels of GFP fluorescence regardless of the presence of Her2-scFv or antigen. This suggests that the Srt.bbz receptor was providing activation signals to the Jurkat cells by binding to the Her2-positive target cells via the Her2-scFv recognition molecule. It was then tested whether the TCR signaling provided by the Srt.bbz receptor was sufficient to induce killing of target cells.

Figure 5A:
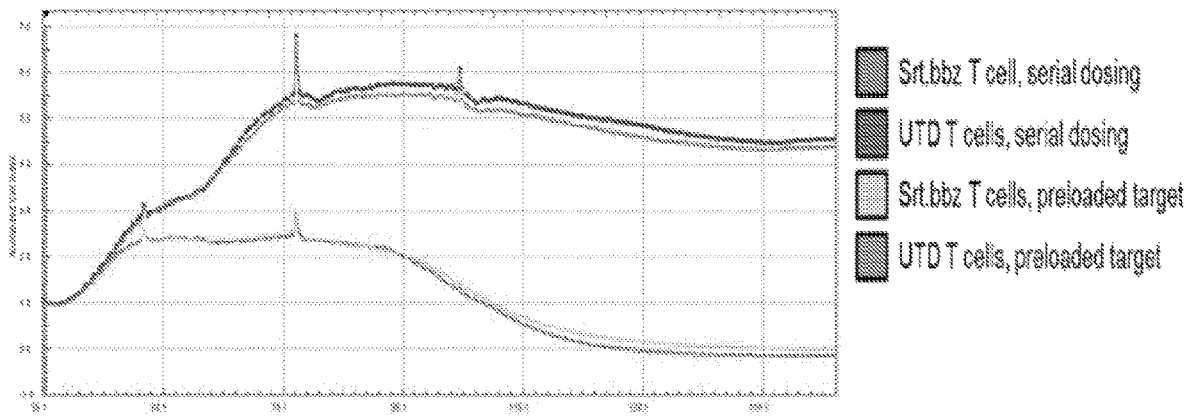
FIGS. 5A-5C are a series of graphs showing that targeted cell killing by Srt.bbz T cells is managed through scFv administration. Primary human T cells were transduced with Srt.bbz and their ability to lyse Her2-positive SKOV3 tumor cells was measured using an Xcelligence cell killing assay. The number of tumor cells per well was normalized according to pretreatment readings and the amount of living tumor cells is represented by the normalized cell index (y-axis) measured over time in hours (x-axis).
Figure 5B:
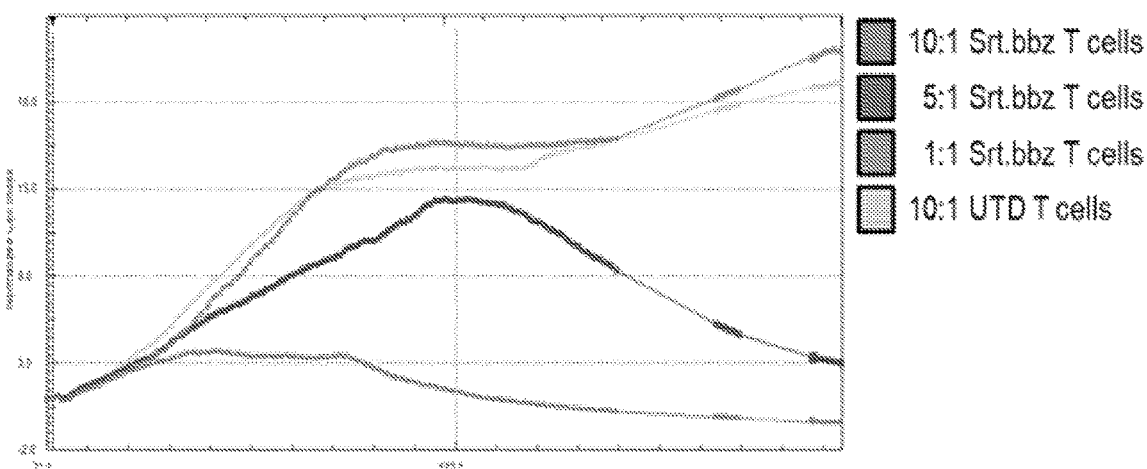
Figure 5C:
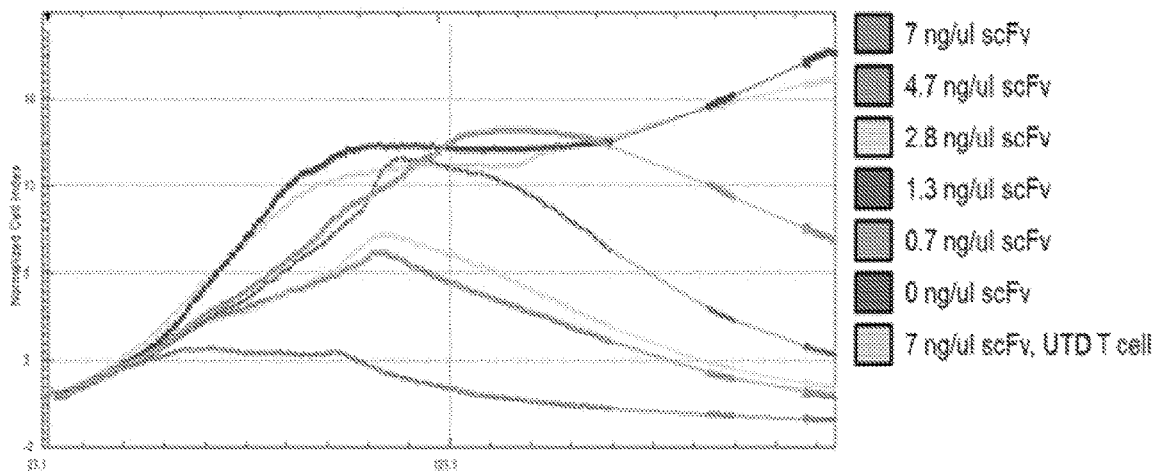

Primary human T cells, which are functionally cytolytic, were engineered to express the Srt.bbz receptor and then were either ARMed or unARMed (i.e. with or without Her2-scFv, respectively) and subsequently added to Her2-positive tumor cells. Tumor cell lysis was measured using an Xcelligence cell killing assay. The number of tumor cells per well was normalized according to pretreatment readings and the amount of living tumor cells is represented by the normalized cell index (y-axis) measured over time in hours (x-axis) (FIGS. 5A-5C). Tumor cell lysis was observed with the ARMed Srt.bbz T cells but neither with the unARMed Srt.bbz T cells nor with the untransduced T cells that had Her2-scFv (FIG. 5A). ARMed Srt.bbz T cell killing was found to occur in a dose dependent manner in titrations of both effector to target (E: T) ratios (FIG. 5B) and in Her2-scFv concentrations (FIG. 5C).

Figure 6:
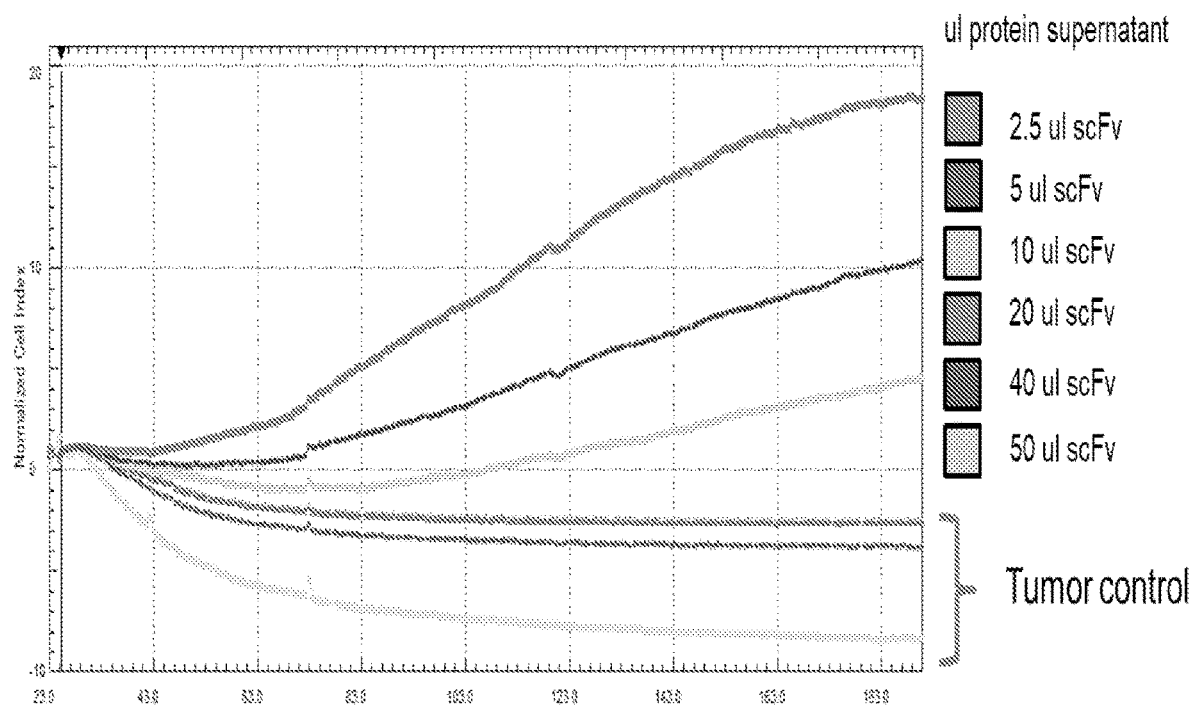
FIG. 6 is a graph showing that Srt.bbz T cells can kill CAOV3 cells by targeting EGFR antigen and killing is dose-dependent on scFv administration. Primary human T cells were transduced with Srt.bbz and their ability to lyse EGFR-positive CAOV3 tumor cells was measured using an Xcelligence cell killing assay. The number of tumor cells per well was normalized according to pretreatment readings and the amount of living tumor cells is represented by the normalized cell index (y-axis) measured over time in hours (x-axis). Sortase-compatible EGFR scFv was administered once at the volumes shown at the same time T cells were added.

Next, Srt.bbz T cells were tested for their ability to target and kill a different tumor cell line using a sortase-compatible scFv that recognizes a different tumor antigen. Primary human T cells were transduced with Srt.bbz and their ability to lyse an EGFR-positive CAOV3 tumor cells was measured using a single dose of EGFR scFv at the dosages shown (FIG. 6), which was added just prior to the SIR T cells. Srt.bbz T cells were shown to be cytolytic for CAOV3 cells, but only when ARMed with anti-EGFR scFv, and killing was dose-dependent on scFv administration (FIG. 6).

The specificity of target cells was improved by using combinations of scFvs, as demonstrated by cell killing assays (FIGS. 7A-7B). The scFv protein was produced in cell culture and the volume of the supernatant containing the scFv is shown for each cell killing assay (FIGS. 7A-7B). The EGFR+/Her2+ SKOV3 cell was targeted and killed by Srt.bbz T cells when Her2-scFv was added to the cells and then EGFR-scFv was administered the next day. There was no detectable cell killing when a single dose of either scFv was administered at the same concentration (FIG. 7A). Similarly, Srt.bbz killing of EGFR+/MSLN+ CAOV3 cells increased when EGFR-scFv and MSLN-scFv were added in combination versus administering either scFv alone (FIG. 7B).

Figure 8A:
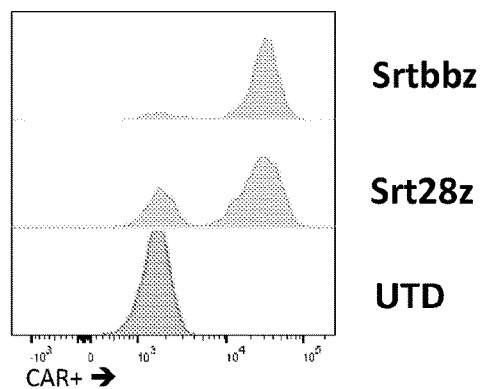
FIGS. 8A-8C are a series of plots showing a comparison of CAR intracellular signaling domains 4-1BB (Srtbbz) and CD28 (Srt28z).
Figure 8B:
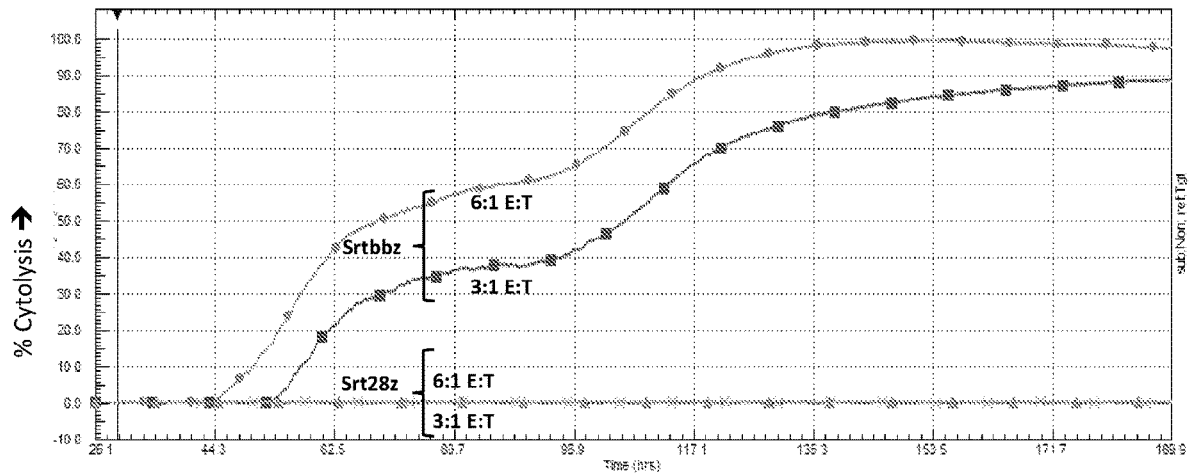
Figure 8C:
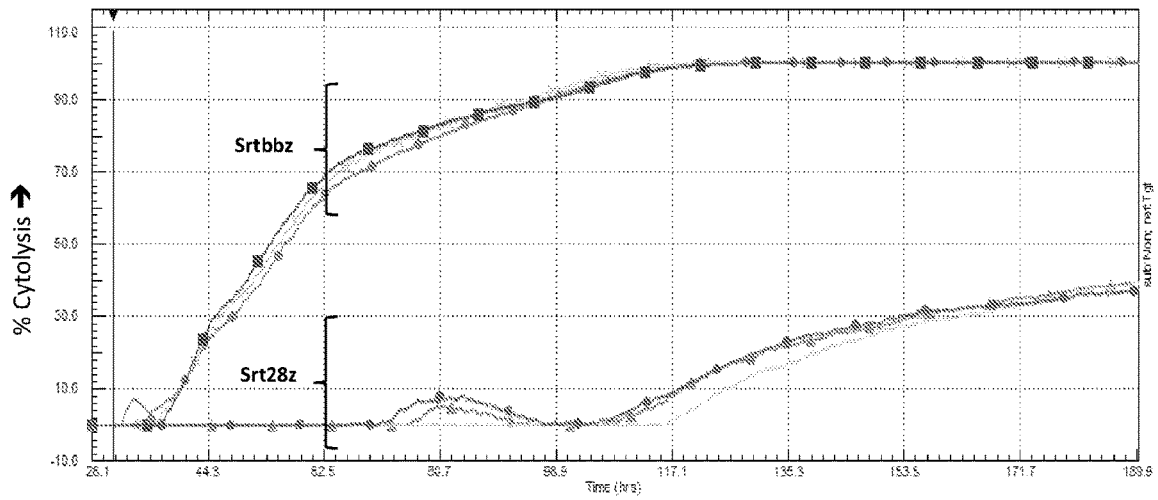

A comparison of CAR intracellular signaling domains 4-1BB (Srt.bbz) and CD28 (Srt.28z) is shown in FIGS. 8A-8C. Primary T cells were engineered with a sortase immune receptor that contained either a 4-1BB or CD28 signaling domain. The T cell surface expression of Srt.bbz and Srt.28z was identified by flow cytometry using a sortase-recognition motif probe, which showed similar levels of expression between the two receptors (FIG. 8A). The cytotoxicity of Srt.bbz and Srt.28z was compared in a cell killing assay using Her2+ SKOV3 cells that were incubated with Her2-scFv and then washed to remove excess scFv (i.e. preloaded). The SIR-T cells were then added at two different E: T ratios, which demonstrated a higher percent lysis of the SKOV3 cells by the Srt.bbz cells versus the Srt.28z (FIG. 8B). Similarly, Srt.bbz and Srt.28z were compared for their ability to lyse SKOV3 cells at a 6:1 E: T when Her2-scFv was added in a single dose along with the T cells, which showed better anti-tumor efficacy in the Srt.bbz T cells than the Srt.28z T cells (FIG. 8C).

Figure 9A:
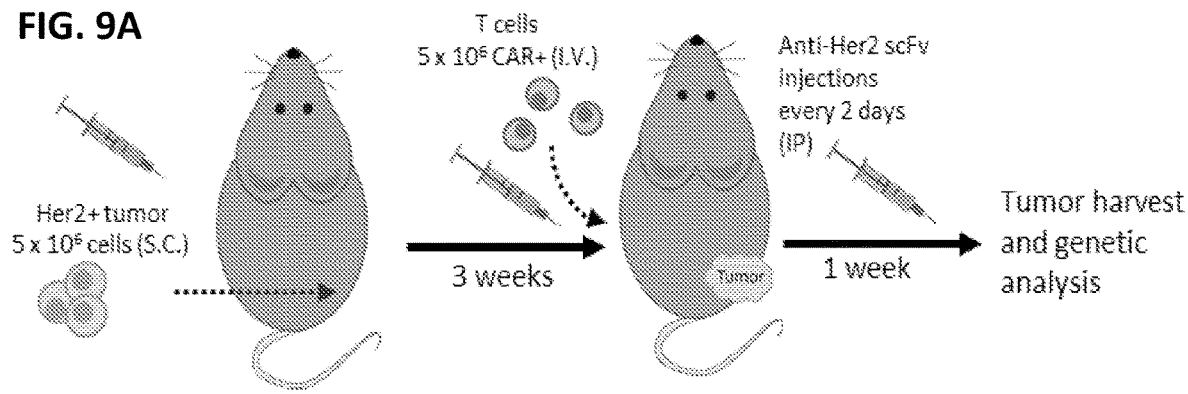
FIGS. 9A-9D are a series of graphs and images illustrating that ARMed SIR-T cells infiltrate tumors in vivo.
Figure 9B:
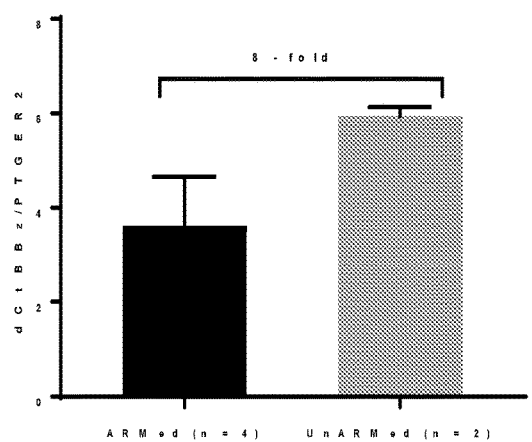
Figure 9C:
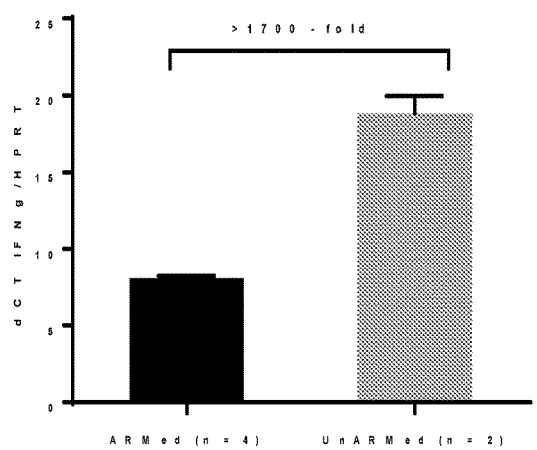
Figure 9D:
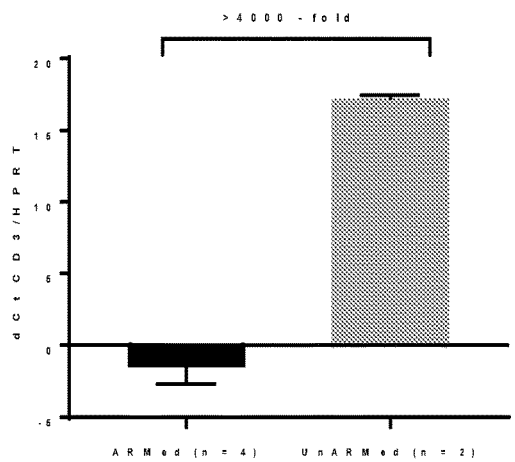

ARMed SIR-T cells infiltrated tumors in vivo (FIGS. 9A-9D). To demonstrate that SIR-T cells can infiltrate tumors in vivo, mice with subcutaneous (S.C.) SKOV3 xenografts were infused with Srt.bbz T cells intravenously (I.V.). The mice were then intraperitoneally (I.P.) injected every other day with Her2-scFv for one week and then tumors were harvested for genetic analysis by real-time PCR (FIG. 9A). Real-time PCR data is represented by deltaCt (dCt) where a lower dCt corresponds to higher quantities of DNA or RNA template (FIGS. 9B-9D). The amount of Srt.bbz DNA in tumor tissue was measured using a Taqman assay that detects DNA for the CAR intracellular domain and this was normalized to mouse genomic DNA using an assay for mouse PTGER2 DNA (FIG. 9B). This assay demonstrated an enrichment of Srt.bbz T cell DNA in the tumor when mice were injected with the targeting Her2-scFv versus without Her2-scFv. The relative expression of the human T cell activation cytokine, IFNgamma was detected in the tumor xenografts using a Taqman expression assay that was normalized to the mouse HPRT housekeeping gene, and this assay showed higher levels of expression in the mice that received the Her2-scFv versus those that did not (FIG. 9C). Another Taqman assay was used to detect the relative tumor expression of human CD3epsilon normalized to mouse HPRT expression and this also showed higher levels of expression in the mice that received the Her2-scFv versus those that did not (FIG. 9D).

Figure 10A:
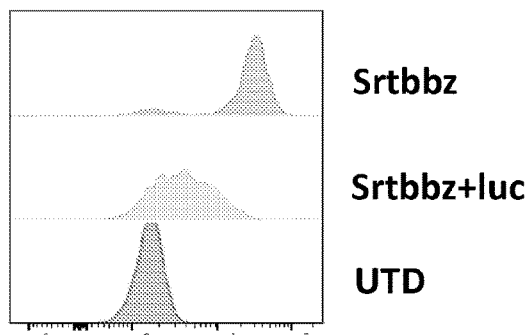
FIGS. 10A-10C are a series of plots showing comparison of cytotoxicity between Srtbbz with or without luciferase expression, which is used to image T cells in vivo.
Figure 10B:
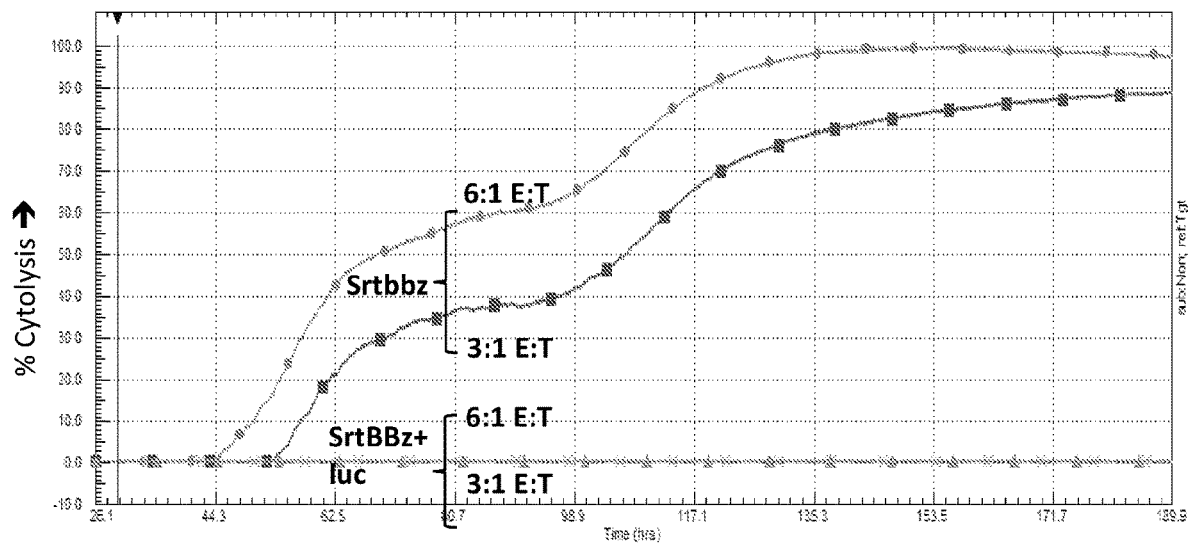
Figure 10C:
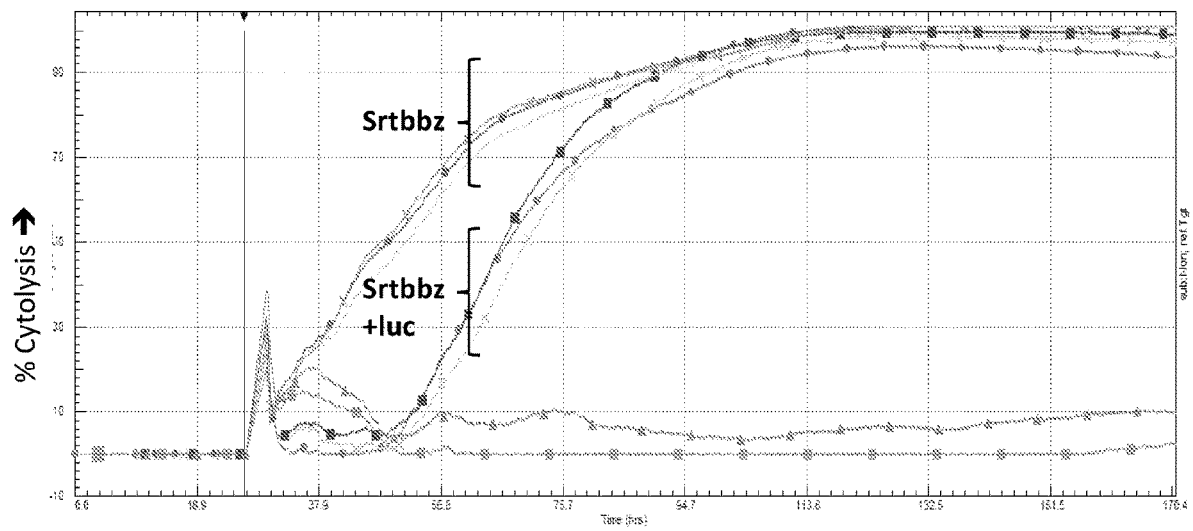

T cells were engineered to co-express Srt.bbz and a luciferase reporter gene (Srt.bbz+luc) so they could be monitored by in vivo imaging The surface expression of Srt.bbz was compared by flow cytometry in Srt.bbz+luc versus Srt.bbz-only T cells and it was shown that Srt.bbz+luc T cells had less Srt.bbz expression (FIG. 10A). A cytotoxicity assay was performed with Her2+SKOV3 target cells and Her2-scFv to determine if there was a difference in cytotoxicity between Srt.bbz and Srt.bbz+luc T cells. In one cytotoxicity assay, Her2-scFv was preloaded on to SKOV3 cells and Srt.bbz or Srt.bbz+luc was added at E: T ratios of 6:1 or 3:1, which showed cytotoxicity of the target cells by the Srtbbz T cells but not by the Srt.bbz+luc T cells (FIG. 10B). In another cytotoxicity assay, Her2-scFv was added once prior to the addition of T cells at a 6:1 E: T and this showed that both SIR-T cell products lysed the target cells although the Srt.bbz T cells produced more potent cytotoxicity than the Srt.bbz+luc T cells (FIG. 10C). Negative controls consisting of scFv without SIR-T cells or SIR-T cells without scFv did not cause target cytotoxicity.

Figure 11A:
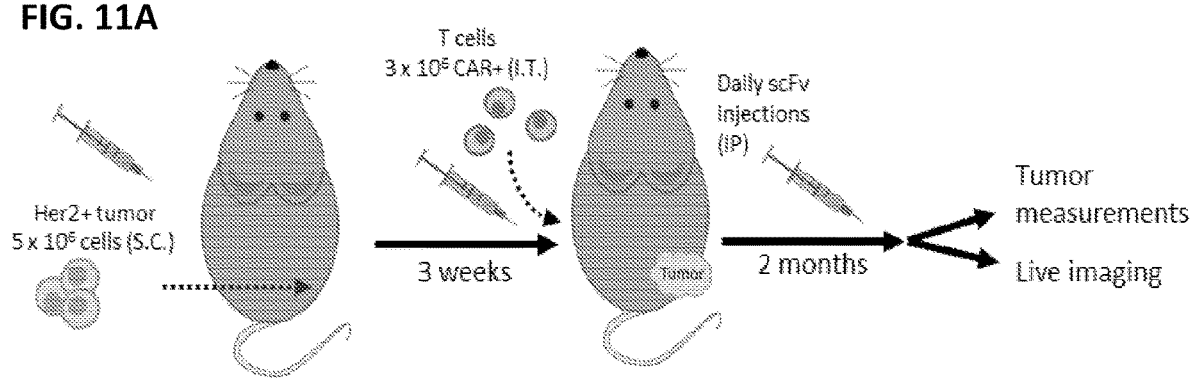
FIGS. 11A-11C are a series of plots and images illustrating that Srtbbz can control tumors in vivo.
Figure 11B:
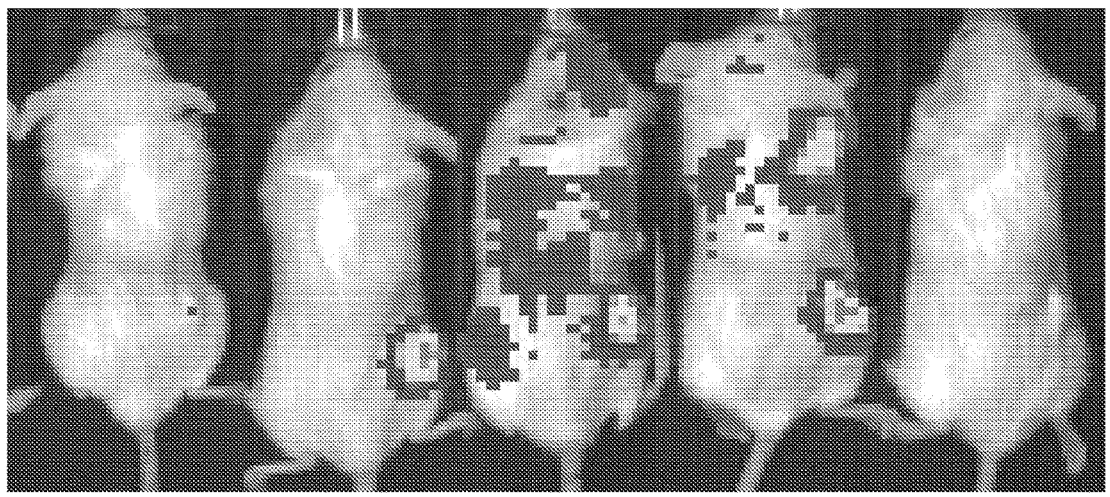
Figure 11C:
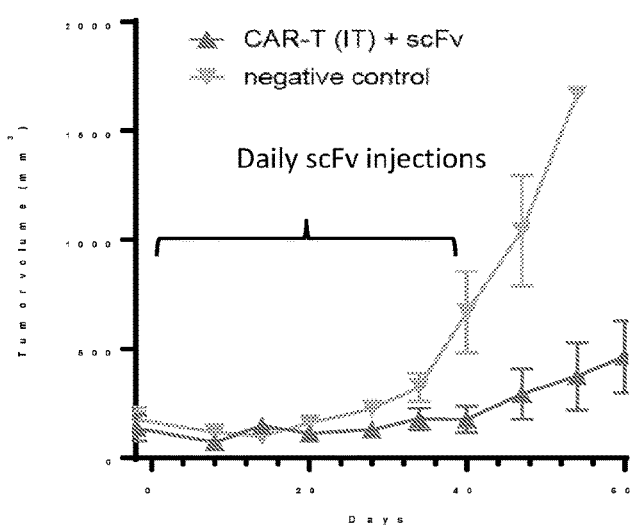

To demonstrate that Srt.bbz T cells can control tumors in vivo, mice were engrafted S.C. with Her2+SKOV3 target cells, then Srt.bbz+luc T cells were intratumorally (I.T.) injected and Her2-scFv was I.P. injected every other day for 40 days (FIG. 11A). Srt.bbz+luc T cells were observed in the tumors of all 5 of the mice via in vivo imaging. IVIS imaging of mice 18 days post Srt.bbz+luc injection are shown (FIG. 11B). Tumor control was maintained for the duration of Her2-scFv injections but not in negative control mice, which received no T cell or scFv injections (FIG. 11C).

Example 2: Overview

It was demonstrated herein that antigen targeting by Srt.bbz T cells can be directed through the addition of sortase-compatible ARMs and that once activated, the Srt.bbz T cells can kill tumor cells in vitro and in vivo. Specifically, Srt.bbz T cells killed Her2-positive tumor cells in the presence of sortase-compatible Her2-scFv. These "switchable" Str.bbz T cells provide two main advantages over conventional CAR T cell therapy. First, "switchable" CARs are safer since the initiation and cessation of T cell therapy can be controlled via ARM dosing or withdrawal. Second, antigenic escape by tumors can be overcome using multiple ARMs to target different tumor clonal populations. As shown herein, the degree of ARMed Srt.bbz T cell killing of Her2-positive tumor cells can be controlled by the concentration of sortase-compatible scFvs. Srt.bbz T cell killing can also be retargeted to different tumor cells by using different sortase-compatible scFvs that recognize different tumor antigens.

Figure 12:
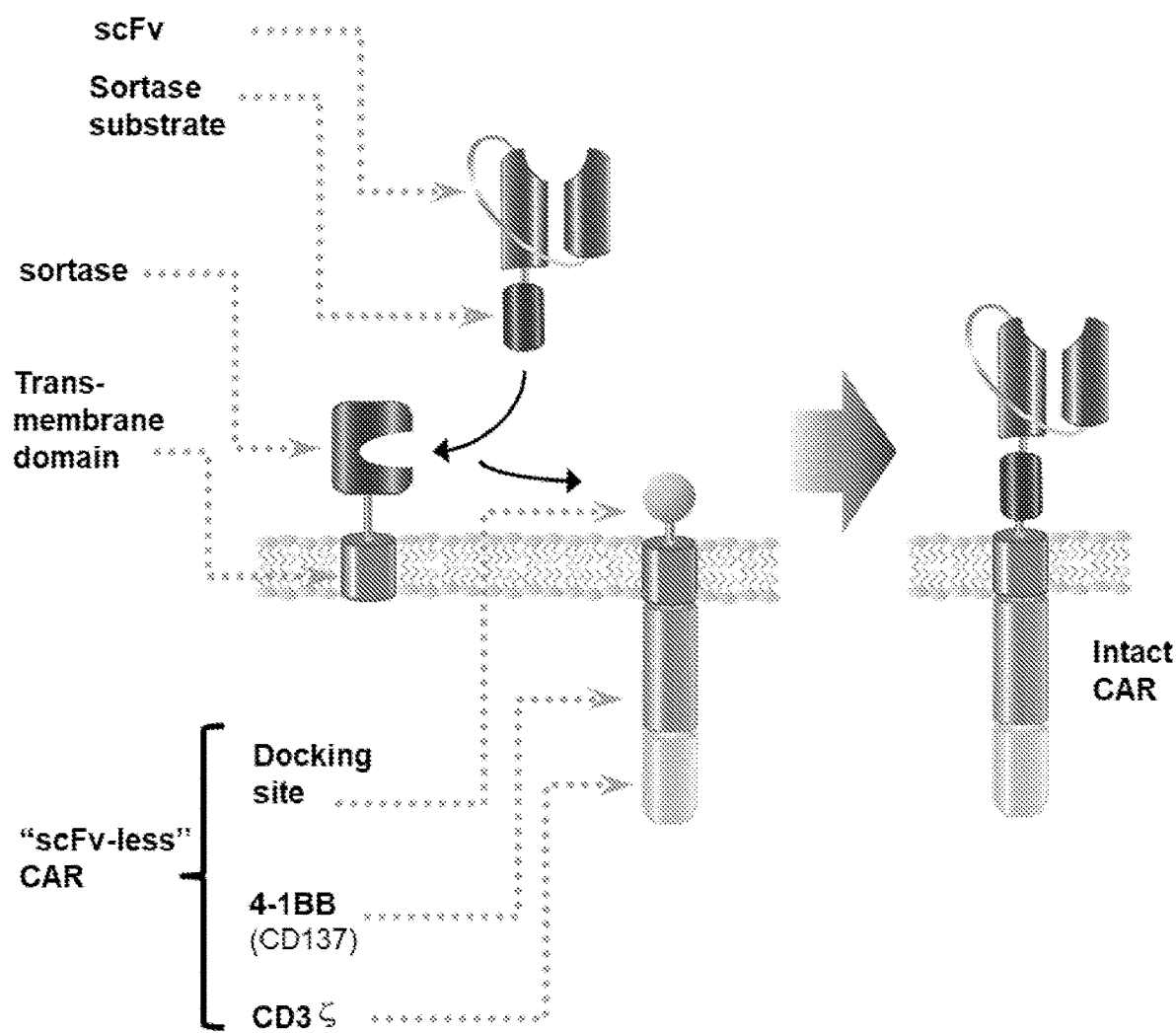
FIG. 12 is a diagram depicting the design of a two-part switchable receptor system. An alternative design for a sortase immune receptor is to express the sortase enzyme and the intracellular signaling domains (ICD) on separate membrane anchored proteins. The extracellular sortase protein captures sortase-compatible molecules, such as a probe or scFv, and covalently binds it to a compatible docking site on the extracellular portion of the ICD protein.

In addition, a two-part sortase system was designed where the sortase enzyme is on a separate protein from the intracellular signaling domains (ICD) (FIG. 12). In this configuration, T cells co-express the membrane-bound, extracellular sortase enzyme and the membrane-bound ICD, which acts as a docking site for a sortase-compatible ARM. This system differs from the previously described system in that the ARM is covalently bound to the ICD protein and thus it reduces the ICD-ARM off-rate. Also, the ARM binds directly to the ICD protein without having the sortase enzyme in between the two motifs. This results in an overall shorter receptor, which may improve T cell killing since the hinge length of a CAR is known to impact its function. Another design consideration is to reduce the immunogenicity of sortase. Since sortases are of bacterial origin, sortase-expressing T cells may be eliminated by a patient's own immune system. One method for reducing this is to make sortase expression transient using an inducible promoter. The inducing drug is administered at the same time as ARM infusion so that sortase expression coincides with high intratumoral ARM concentrations.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A sortase immune receptor comprising, from N-terminus to C-terminus:
   - a sortase enzymatic region;
   - a transmembrane domain; and
   - an intracellular domain.

2. The sortase immune receptor of claim 1, wherein the sortase enzymatic region is derived from a sortase or a variant thereof.

3. The sortase immune receptor of claim 2, wherein the sortase is sortase A or a variant thereof.

4. The sortase enzymatic region of claim 2, wherein the variant thereof is a calcium-independent sortase variant.

5. The sortase immune receptor of claim 2, wherein the variant thereof is a truncated sortase.

6. The sortase immune receptor of claim 5, wherein the truncated sortase is a truncated sortase A.

7. The sortase immune receptor of claim 1, wherein the intracellular domain comprises a costimulatory domain and an intracellular signaling domain.

8. A modified T cell comprising the sortase immune receptor of claim 1.

9. A method for treating a disease or disorder in a subject in need thereof, the method comprising:
   administering to the subject a therapeutically effective amount of a composition comprising an engineered T cell comprising a sortase immune receptor and antigen-binding sortase substrate, wherein the sortase immune receptor comprises:
   - a sortase enzymatic region;
   - a transmembrane domain; and
   - an intracellular domain,
   and wherein the antigen-binding sortase substrate comprises
   - an antigen-binding domain; and
   - a sortase recognition motif.

10. The method of claim 9, wherein the disease is cancer.

11. The method of claim 10, wherein the antigen-binding domain comprises a Her2 scFv.

12. The method of claim 9, wherein the disease is an autoimmune disease or disorder.

13. The method of claim 9, wherein the antigen-binding sortase substrate is switchable with a second antigen-binding sortase substrate comprising a second antigen binding domain fused to a second sortase recognition motif.

14. The method of claim 9, wherein the dosage of the therapeutically effective amount of the antigen-binding sortase substrate is increased or decreased.

15. The method of claim 9, further comprising administering a second sortase CAR, and/or a second sortase immune receptor and/or a second antigen-binding sortase substrate, wherein the antigen binding domain of the CAR and/or the antigen-binding sortase substrate is different from the first CAR and/or the antigen-binding sortase substrate.

* * * * *

SEQUENCE LISTING

<160> NUMBER OF SEQ ID NOS: 114

<210> SEQ ID NO 1
<211> LENGTH: 206
<212> TYPE: PRT
<213> ORGANISM: Staphylococcus aureus

<400> SEQUENCE: 1

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Asn Lys Gln Gln Ala Lys Pro Gln
50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
130                 135                 140

Lys Val Gly Asn Glu Thr Arg Lys Tyr Lys Met Thr Ser Ile Arg Asp
145                 150                 155                 160

Val Lys Pro Thr Asp Val Glu Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
        195                 200                 205

<210> SEQ ID NO 2
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

Leu Pro Xaa Thr Gly
1               5

<210> SEQ ID NO 3
<211> LENGTH: 5
<212> TYPE: PRT
<213> ORGANISM: Artificial Sequence
<220> FEATURE:
<223> OTHER INFORMATION: sortase recognition motif

<400> SEQUENCE: 3

Leu Pro Glu Thr Gly
1               5

```
<210> SEQ ID NO 4
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 4

Leu Pro Xaa Thr Xaa
1               5

<210> SEQ ID NO 5
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: X
<222> LOCATION: (1)..(1)
<223> OTHER INFORMATION: Xaa is L or I
<220> FEATURE:
<221> NAME/KEY: X
<222> LOCATION: (2)..(2)
<223> OTHER INFORMATION: Xaa is P or G
<220> FEATURE:
<221> NAME/KEY: X
<222> LOCATION: (3)..(3)
<223> OTHER INFORMATION: Xaa is T or A
<220> FEATURE:
<221> NAME/KEY: misc_feature
<222> LOCATION: (4)..(5)
<223> OTHER INFORMATION: Xaa can be any naturally occurring amino acid

<400> SEQUENCE: 5

Xaa Xaa Xaa Xaa Xaa
1               5

<210> SEQ ID NO 6
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: X
<222> LOCATION: (1)..(1)
<223> OTHER INFORMATION: Xaa is L or I
<220> FEATURE:
<221> NAME/KEY: X
<222> LOCATION: (2)..(2)
<223> OTHER INFORMATION: Xaa is P or G
<220> FEATURE:
<221> NAME/KEY: X
<222> LOCATION: (3)..(3)
<223> OTHER INFORMATION: Xaa is K, A, N, E or Q
<220> FEATURE:
<221> NAME/KEY: X
<222> LOCATION: (4)..(4)
<223> OTHER INFORMATION: Xaa is T or A
<220> FEATURE:
<221> NAME/KEY: X
<222> LOCATION: (5)..(5)
<223> OTHER INFORMATION: Xaa is A or G

<400> SEQUENCE: 6
```

```
Xaa Xaa Xaa Xaa Xaa
1               5

<210> SEQ ID NO 7
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: X
<222> LOCATION: (3)..(3)
<223> OTHER INFORMATION: Xaa is K, A, N, E, or Q
<220> FEATURE:
<221> NAME/KEY: misc_feature
<222> LOCATION: (5)..(5)
<223> OTHER INFORMATION: Xaa can be any naturally occurring amino acid

<400> SEQUENCE: 7

Leu Pro Xaa Thr Xaa
1               5

<210> SEQ ID NO 8
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: X
<222> LOCATION: (3)..(3)
<223> OTHER INFORMATION: Xaa is K, A, N, E, or Q

<400> SEQUENCE: 8

Leu Pro Xaa Thr Gly
1               5

<210> SEQ ID NO 9
<211> LENGTH: 5
<212> TYPE: PRT
<213> ORGANISM: Artificial Sequence
<220> FEATURE:
<223> OTHER INFORMATION: sortase recognition motif

<400> SEQUENCE: 9

Leu Pro Lys Thr Gly
1               5

<210> SEQ ID NO 10
<211> LENGTH: 5
<212> TYPE: PRT
<213> ORGANISM: Artificial Sequence
<220> FEATURE:
<223> OTHER INFORMATION: sortase recognition motif

<400> SEQUENCE: 10

Leu Pro Ala Thr Gly
1               5

<210> SEQ ID NO 11
<211> LENGTH: 5
<212> TYPE: PRT
<213> ORGANISM: Artificial Sequence
<220> FEATURE:
<223> OTHER INFORMATION: sortase recognition motif

<400> SEQUENCE: 11

Leu Pro Asn Thr Gly
```

```
1               5

<210> SEQ ID NO 12
<211> LENGTH: 5
<212> TYPE: PRT
<213> ORGANISM: Artificial Sequence
<220> FEATURE:
<223> OTHER INFORMATION: sortase recognition motif

<400> SEQUENCE: 12

Leu Pro Glu Thr Gly
1               5

<210> SEQ ID NO 13
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 13

Leu Pro Xaa Ala Gly
1               5

<210> SEQ ID NO 14
<211> LENGTH: 5
<212> TYPE: PRT
<213> ORGANISM: Artificial Sequence
<220> FEATURE:
<223> OTHER INFORMATION: sortase recognition motif

<400> SEQUENCE: 14

Leu Pro Asn Ala Gly
1               5

<210> SEQ ID NO 15
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 15

Leu Pro Xaa Thr Ala
1               5

<210> SEQ ID NO 16
<211> LENGTH: 5
<212> TYPE: PRT
<213> ORGANISM: Artificial Sequence
<220> FEATURE:
<223> OTHER INFORMATION: sortase recognition motif

<400> SEQUENCE: 16

Leu Pro Asn Thr Ala
1               5

<210> SEQ ID NO 17
<211> LENGTH: 5
<212> TYPE: PRT
```

```
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 17

Leu Gly Xaa Thr Gly
1               5

<210> SEQ ID NO 18
<211> LENGTH: 5
<212> TYPE: PRT
<213> ORGANISM: Artificial Sequence
<220> FEATURE:
<223> OTHER INFORMATION: sortase recognition motif

<400> SEQUENCE: 18

Leu Gly Ala Thr Gly
1               5

<210> SEQ ID NO 19
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 19

Ile Pro Xaa Thr Gly
1               5

<210> SEQ ID NO 20
<211> LENGTH: 5
<212> TYPE: PRT
<213> ORGANISM: Artificial Sequence
<220> FEATURE:
<223> OTHER INFORMATION: sortase recognition motif

<400> SEQUENCE: 20

Ile Pro Asn Thr Gly
1               5

<210> SEQ ID NO 21
<211> LENGTH: 5
<212> TYPE: PRT
<213> ORGANISM: Artificial Sequence
<220> FEATURE:
<223> OTHER INFORMATION: sortase recognition motif

<400> SEQUENCE: 21

Ile Pro Glu Thr Gly
1               5

<210> SEQ ID NO 22
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: X
<222> LOCATION: (2)..(2)
```

```
<223> OTHER INFORMATION: Xaa is P, A or S
<220> FEATURE:
<221> NAME/KEY: X
<222> LOCATION: (3)..(3)
<223> OTHER INFORMATION: Xaa is T or S
<220> FEATURE:
<221> NAME/KEY: misc_feature
<222> LOCATION: (4)..(5)
<223> OTHER INFORMATION: Xaa can be any naturally occurring amino acid

<400> SEQUENCE: 22

Asn Xaa Xaa Xaa Xaa
1               5

<210> SEQ ID NO 23
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: X
<222> LOCATION: (2)..(2)
<223> OTHER INFORMATION: Xaa is P, A or S
<220> FEATURE:
<221> NAME/KEY: X
<222> LOCATION: (3)..(3)
<223> OTHER INFORMATION: Xaa is Q or K
<220> FEATURE:
<221> NAME/KEY: X
<222> LOCATION: (4)..(4)
<223> OTHER INFORMATION: Xaa is T or S
<220> FEATURE:
<221> NAME/KEY: X
<222> LOCATION: (5)..(5)
<223> OTHER INFORMATION: Xaa is A, H, N, G, or S

<400> SEQUENCE: 23

Asn Xaa Xaa Xaa Xaa
1               5

<210> SEQ ID NO 24
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 24

Asn Pro Xaa Thr Xaa
1               5

<210> SEQ ID NO 25
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: X
<222> LOCATION: (3)..(3)
<223> OTHER INFORMATION: Xaa is Q or K
<220> FEATURE:
<221> NAME/KEY: X
<222> LOCATION: (5)..(5)
```

```
<223> OTHER INFORMATION: Xaa is H, N, G, or S

<400> SEQUENCE: 25

Asn Pro Xaa Thr Xaa
1               5

<210> SEQ ID NO 26
<211> LENGTH: 5
<212> TYPE: PRT
<213> ORGANISM: Artificial Sequence
<220> FEATURE:
<223> OTHER INFORMATION: sortase recognition motif

<400> SEQUENCE: 26

Asn Pro Gln Thr Asn
1               5

<210> SEQ ID NO 27
<211> LENGTH: 5
<212> TYPE: PRT
<213> ORGANISM: Artificial Sequence
<220> FEATURE:
<223> OTHER INFORMATION: sortase recognition motif

<400> SEQUENCE: 27

Asn Pro Lys Thr Gly
1               5

<210> SEQ ID NO 28
<211> LENGTH: 5
<212> TYPE: PRT
<213> ORGANISM: Artificial Sequence
<220> FEATURE:
<223> OTHER INFORMATION: sortase recognition motif

<400> SEQUENCE: 28

Asn Ser Lys Thr Ala
1               5

<210> SEQ ID NO 29
<211> LENGTH: 5
<212> TYPE: PRT
<213> ORGANISM: Artificial Sequence
<220> FEATURE:
<223> OTHER INFORMATION: sortase recognition motif

<400> SEQUENCE: 29

Asn Pro Gln Thr Gly
1               5

<210> SEQ ID NO 30
<211> LENGTH: 5
<212> TYPE: PRT
<213> ORGANISM: Artificial Sequence
<220> FEATURE:
<223> OTHER INFORMATION: sortase recognition motif

<400> SEQUENCE: 30

Asn Ala Lys Thr Asn
1               5

<210> SEQ ID NO 31
<211> LENGTH: 5
<212> TYPE: PRT
<213> ORGANISM: Artificial Sequence
<220> FEATURE:
<223> OTHER INFORMATION: sortase recognition motif
```

<400> SEQUENCE: 31

Asn Pro Gln Ser Ser
1               5

<210> SEQ ID NO 32
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 32

Leu Pro Xaa Thr Xaa
1               5

<210> SEQ ID NO 33
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: X
<222> LOCATION: (3)..(3)
<223> OTHER INFORMATION: Xaa is K, S, E, L, A or N

<400> SEQUENCE: 33

Leu Pro Xaa Thr Gly
1               5

<210> SEQ ID NO 34
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 34

Leu Ala Xaa Thr Gly
1               5

<210> SEQ ID NO 35
<211> LENGTH: 5
<212> TYPE: PRT
<213> ORGANISM: Artificial Sequence
<220> FEATURE:
<223> OTHER INFORMATION: sortase recognition motif

<400> SEQUENCE: 35

Leu Pro Ile Thr Gly
1               5

<210> SEQ ID NO 36
<211> LENGTH: 5
<212> TYPE: PRT
<213> ORGANISM: Artificial Sequence

```
<220> FEATURE:
<223> OTHER INFORMATION: sortase recognition motif

<400> SEQUENCE: 36

Leu Pro Asp Thr Ala
1               5

<210> SEQ ID NO 37
<211> LENGTH: 5
<212> TYPE: PRT
<213> ORGANISM: Artificial Sequence
<220> FEATURE:
<223> OTHER INFORMATION: sortase recognition motif

<400> SEQUENCE: 37

Leu Pro Leu Thr Gly
1               5

<210> SEQ ID NO 38
<211> LENGTH: 5
<212> TYPE: PRT
<213> ORGANISM: Artificial Sequence
<220> FEATURE:
<223> OTHER INFORMATION: sortase recognition motif

<400> SEQUENCE: 38

Leu Pro Met Thr Gly
1               5

<210> SEQ ID NO 39
<211> LENGTH: 5
<212> TYPE: PRT
<213> ORGANISM: Artificial Sequence
<220> FEATURE:
<223> OTHER INFORMATION: sortase recognition motif

<400> SEQUENCE: 39

Leu Pro Gln Thr Ser
1               5

<210> SEQ ID NO 40
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 40

Leu Ala Xaa Thr Xaa
1               5

<210> SEQ ID NO 41
<211> LENGTH: 5
<212> TYPE: PRT
<213> ORGANISM: Artificial Sequence
<220> FEATURE:
<223> OTHER INFORMATION: sortase recognition motif

<400> SEQUENCE: 41

Leu Ala Glu Thr Gly
```

```
1               5

<210> SEQ ID NO 42
<211> LENGTH: 5
<212> TYPE: PRT
<213> ORGANISM: Artificial Sequence
<220> FEATURE:
<223> OTHER INFORMATION: sortase recognition motif

<400> SEQUENCE: 42

Leu Ala Ala Thr Gly
1               5

<210> SEQ ID NO 43
<211> LENGTH: 5
<212> TYPE: PRT
<213> ORGANISM: Artificial Sequence
<220> FEATURE:
<223> OTHER INFORMATION: sortase recognition motif

<400> SEQUENCE: 43

Leu Ala His Thr Gly
1               5

<210> SEQ ID NO 44
<211> LENGTH: 5
<212> TYPE: PRT
<213> ORGANISM: Artificial Sequence
<220> FEATURE:
<223> OTHER INFORMATION: sortase recognition motif

<400> SEQUENCE: 44

Leu Ala Ser Thr Gly
1               5

<210> SEQ ID NO 45
<211> LENGTH: 5
<212> TYPE: PRT
<213> ORGANISM: Artificial Sequence
<220> FEATURE:
<223> OTHER INFORMATION: sortase recognition motif

<400> SEQUENCE: 45

Leu Ala Phe Thr Gly
1               5

<210> SEQ ID NO 46
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 46

Leu Pro Xaa Ala Xaa
1               5

<210> SEQ ID NO 47
<211> LENGTH: 5
<212> TYPE: PRT
```

```
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 47

Leu Ala Xaa Thr Xaa
1               5

<210> SEQ ID NO 48
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 48

Leu Gly Xaa Thr Xaa
1               5

<210> SEQ ID NO 49
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 49

Ile Pro Xaa Thr Xaa
1               5

<210> SEQ ID NO 50
<211> LENGTH: 5
<212> TYPE: PRT
<213> ORGANISM: Artificial Sequence
<220> FEATURE:
<223> OTHER INFORMATION: sortase recognition motif

<400> SEQUENCE: 50

Ile Pro Gln Thr Gly
1               5

<210> SEQ ID NO 51
<211> LENGTH: 5
<212> TYPE: PRT
<213> ORGANISM: Artificial Sequence
<220> FEATURE:
<223> OTHER INFORMATION: sortase recognition motif
```

```
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 51

Asn Pro Xaa Thr Xaa
1               5

<210> SEQ ID NO 52
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (5)..(5)
<223> OTHER INFORMATION: Xaa can be any naturally occurring amino acid

<400> SEQUENCE: 52

Asn Pro Gln Ser Xaa
1               5

<210> SEQ ID NO 53
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (5)..(5)
<223> OTHER INFORMATION: Xaa can be any naturally occurring amino acid

<400> SEQUENCE: 53

Asn Ser Lys Thr Xaa
1               5

<210> SEQ ID NO 54
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (5)..(5)
<223> OTHER INFORMATION: Xaa can be any naturally occurring amino acid

<400> SEQUENCE: 54

Asn Pro Gln Thr Xaa
1               5

<210> SEQ ID NO 55
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: misc_feature
<222> LOCATION: (5)..(5)
<223> OTHER INFORMATION: Xaa can be any naturally occurring amino acid

<400> SEQUENCE: 55
```

Asn Ala Lys Thr Xaa
1               5

<210> SEQ ID NO 56
<211> LENGTH: 5
<212> TYPE: PRT
<213> ORGANISM: Artificial Sequence
<220> FEATURE:
<223> OTHER INFORMATION: sortase recognition motif

<400> SEQUENCE: 56

Leu Ser Arg Thr Gly
1               5

<210> SEQ ID NO 57
<211> LENGTH: 5
<212> TYPE: PRT
<213> ORGANISM: Artificial Sequence
<220> FEATURE:
<223> OTHER INFORMATION: sortase recognition motif

<400> SEQUENCE: 57

Ser Pro Lys Thr Gly
1               5

<210> SEQ ID NO 58
<211> LENGTH: 5
<212> TYPE: PRT
<213> ORGANISM: Artificial Sequence
<220> FEATURE:
<223> OTHER INFORMATION: sortase recognition motif

<400> SEQUENCE: 58

Val Pro Asp Thr Gly
1               5

<210> SEQ ID NO 59
<211> LENGTH: 5
<212> TYPE: PRT
<213> ORGANISM: Artificial Sequence
<220> FEATURE:
<223> OTHER INFORMATION: sortase recognition motif

<400> SEQUENCE: 59

Tyr Pro Arg Arg Gly
1               5

<210> SEQ ID NO 60
<211> LENGTH: 5
<212> TYPE: PRT
<213> ORGANISM: Artificial Sequence
<220> FEATURE:
<223> OTHER INFORMATION: sortase recognition motif

<400> SEQUENCE: 60

Gln Val Pro Thr Gly
1               5

<210> SEQ ID NO 61
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: X
<222> LOCATION: (1)..(1)
<223> OTHER INFORMATION: Xaa is L, N, I, Y, Q, V, or S

```
<220> FEATURE:
<221> NAME/KEY: X
<222> LOCATION: (2)..(2)
<223> OTHER INFORMATION: Xaa is P, G, A, S, or V
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: X
<222> LOCATION: (4)..(4)
<223> OTHER INFORMATION: Xaa is T, A, S, or R
<220> FEATURE:
<221> NAME/KEY: misc_feature
<222> LOCATION: (5)..(5)
<223> OTHER INFORMATION: Xaa can be any naturally occurring amino acid

<400> SEQUENCE: 61

Xaa Xaa Xaa Xaa Xaa
1               5

<210> SEQ ID NO 62
<211> LENGTH: 156
<212> TYPE: PRT
<213> ORGANISM: Staphylococcus aureus

<400> SEQUENCE: 62

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
                20                  25                  30

Pro Ala Thr Arg Glu Gln Leu Asn Arg Gly Val Ser Phe Ala Lys Glu
            35                  40                  45

Asn Gln Ser Leu Asp Asp Gln Asn Ile Ser Ile Ala Gly His Thr Phe
        50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Ala Val Glu Val Leu Asp
            100                 105                 110

Glu Gln Lys Gly Lys Asp Lys Gln Leu Thr Leu Ile Thr Cys Asp Asp
        115                 120                 125

Tyr Asn Glu Glu Thr Gly Val Trp Glu Thr Arg Lys Ile Phe Val Ala
130                 135                 140

Thr Glu Val Lys Leu Glu His His His His His His
145                 150                 155

<210> SEQ ID NO 63
<211> LENGTH: 4
<212> TYPE: PRT
<213> ORGANISM: Artificial Sequence
<220> FEATURE:
<223> OTHER INFORMATION: hinge
<220> FEATURE:
<221> NAME/KEY: REPEAT
<222> LOCATION: (1)..(4)
<223> OTHER INFORMATION: repeat n times, wherein n is an integer of at
      least one

<400> SEQUENCE: 63

Gly Gly Gly Ser
1
```

```
<210> SEQ ID NO 64
<211> LENGTH: 4
<212> TYPE: PRT
<213> ORGANISM: Artificial Sequence
<220> FEATURE:
<223> OTHER INFORMATION: hinge

<400> SEQUENCE: 64

Gly Gly Ser Gly
1

<210> SEQ ID NO 65
<211> LENGTH: 5
<212> TYPE: PRT
<213> ORGANISM: Artificial Sequence
<220> FEATURE:
<223> OTHER INFORMATION: hinge

<400> SEQUENCE: 65

Gly Gly Ser Gly Gly
1               5

<210> SEQ ID NO 66
<211> LENGTH: 5
<212> TYPE: PRT
<213> ORGANISM: Artificial Sequence
<220> FEATURE:
<223> OTHER INFORMATION: hinge

<400> SEQUENCE: 66

Gly Ser Gly Ser Gly
1               5

<210> SEQ ID NO 67
<211> LENGTH: 5
<212> TYPE: PRT
<213> ORGANISM: Artificial Sequence
<220> FEATURE:
<223> OTHER INFORMATION: hinge

<400> SEQUENCE: 67

Gly Ser Gly Gly Gly
1               5

<210> SEQ ID NO 68
<211> LENGTH: 5
<212> TYPE: PRT
<213> ORGANISM: Artificial Sequence
<220> FEATURE:
<223> OTHER INFORMATION: hinge

<400> SEQUENCE: 68

Gly Gly Gly Ser Gly
1               5

<210> SEQ ID NO 69
<211> LENGTH: 5
<212> TYPE: PRT
<213> ORGANISM: Artificial Sequence
<220> FEATURE:
<223> OTHER INFORMATION: hinge

<400> SEQUENCE: 69

Gly Ser Ser Ser Gly
1               5

<210> SEQ ID NO 70
```

```
<211> LENGTH: 5
<212> TYPE: PRT
<213> ORGANISM: Artificial Sequence
<220> FEATURE:
<223> OTHER INFORMATION: hinge

<400> SEQUENCE: 70

Asp Lys Thr His Thr
1               5

<210> SEQ ID NO 71
<211> LENGTH: 4
<212> TYPE: PRT
<213> ORGANISM: Artificial Sequence
<220> FEATURE:
<223> OTHER INFORMATION: hinge

<400> SEQUENCE: 71

Cys Pro Pro Cys
1

<210> SEQ ID NO 72
<211> LENGTH: 15
<212> TYPE: PRT
<213> ORGANISM: Artificial Sequence
<220> FEATURE:
<223> OTHER INFORMATION: hinge

<400> SEQUENCE: 72

Cys Pro Glu Pro Lys Ser Cys Asp Thr Pro Pro Cys Pro Arg
1               5                   10                  15

<210> SEQ ID NO 73
<211> LENGTH: 12
<212> TYPE: PRT
<213> ORGANISM: Artificial Sequence
<220> FEATURE:
<223> OTHER INFORMATION: hinge

<400> SEQUENCE: 73

Glu Leu Lys Thr Pro Leu Gly Asp Thr Thr His Thr
1               5                   10

<210> SEQ ID NO 74
<211> LENGTH: 10
<212> TYPE: PRT
<213> ORGANISM: Artificial Sequence
<220> FEATURE:
<223> OTHER INFORMATION: hinge

<400> SEQUENCE: 74

Lys Ser Cys Asp Lys Thr His Thr Cys Pro
1               5                   10

<210> SEQ ID NO 75
<211> LENGTH: 7
<212> TYPE: PRT
<213> ORGANISM: Artificial Sequence
<220> FEATURE:
<223> OTHER INFORMATION: hinge

<400> SEQUENCE: 75

Lys Cys Cys Val Asp Cys Pro
1               5

<210> SEQ ID NO 76
<211> LENGTH: 7
```

```
<212> TYPE: PRT
<213> ORGANISM: Artificial Sequence
<220> FEATURE:
<223> OTHER INFORMATION: hinge

<400> SEQUENCE: 76

Lys Tyr Gly Pro Pro Cys Pro
1               5

<210> SEQ ID NO 77
<211> LENGTH: 15
<212> TYPE: PRT
<213> ORGANISM: Artificial Sequence
<220> FEATURE:
<223> OTHER INFORMATION: hinge

<400> SEQUENCE: 77

Glu Pro Lys Ser Cys Asp Lys Thr Gly Thr Cys Pro Pro Cys Pro
1               5                   10                  15

<210> SEQ ID NO 78
<211> LENGTH: 12
<212> TYPE: PRT
<213> ORGANISM: Artificial Sequence
<220> FEATURE:
<223> OTHER INFORMATION: hinge

<400> SEQUENCE: 78

Glu Arg Lys Cys Cys Val Glu Cys Pro Pro Cys Pro
1               5                   10

<210> SEQ ID NO 79
<211> LENGTH: 17
<212> TYPE: PRT
<213> ORGANISM: Artificial Sequence
<220> FEATURE:
<223> OTHER INFORMATION: hinge

<400> SEQUENCE: 79

Glu Leu Lys Thr Pro Leu Gly Asp Thr Thr Gly Thr Cys Pro Arg Cys
1               5                   10                  15

Pro

<210> SEQ ID NO 80
<211> LENGTH: 12
<212> TYPE: PRT
<213> ORGANISM: Artificial Sequence
<220> FEATURE:
<223> OTHER INFORMATION: hinge

<400> SEQUENCE: 80

Ser Pro Asn Met Val Pro His Ala His His Ala Gln
1               5                   10

<210> SEQ ID NO 81
<211> LENGTH: 15
<212> TYPE: PRT
<213> ORGANISM: Artificial Sequence
<220> FEATURE:
<223> OTHER INFORMATION: hinge

<400> SEQUENCE: 81

Glu Pro Lys Ser Cys Asp Lys Thr Tyr Thr Cys Pro Pro Cys Pro
1               5                   10                  15

<210> SEQ ID NO 82
```

<211> LENGTH: 404
<212> TYPE: PRT
<213> ORGANISM: Artificial Sequence
<220> FEATURE:
<223> OTHER INFORMATION: sortase immune receptor

<400> SEQUENCE: 82

```
Met Ala Leu Pro Val Thr Ala Leu Leu Leu Pro Leu Ala Leu Leu Leu
1               5                   10                  15

His Ala Ala Arg Pro Met Gln Ala Lys Pro Gln Ile Pro Lys Asp Lys
            20                  25                  30

Ser Lys Val Ala Gly Tyr Ile Glu Ile Pro Asp Ala Asp Ile Lys Glu
        35                  40                  45

Pro Val Tyr Pro Gly Pro Ala Thr Arg Glu Gln Leu Asn Arg Gly Val
    50                  55                  60

Ser Phe Ala Lys Glu Asn Gln Ser Leu Asp Asp Gln Asn Ile Ser Ile
65                  70                  75                  80

Ala Gly His Thr Phe Ile Asp Arg Pro Asn Tyr Gln Phe Thr Asn Leu
                85                  90                  95

Lys Ala Ala Lys Lys Gly Ser Met Val Tyr Phe Lys Val Gly Asn Glu
            100                 105                 110

Thr Arg Lys Tyr Lys Met Thr Ser Ile Arg Asn Val Lys Pro Thr Ala
        115                 120                 125

Val Glu Val Leu Asp Glu Gln Lys Gly Lys Asp Lys Gln Leu Thr Leu
    130                 135                 140

Ile Thr Cys Asp Asp Tyr Asn Glu Glu Thr Gly Val Trp Glu Thr Arg
145                 150                 155                 160

Lys Ile Phe Val Ala Thr Glu Val Lys Leu Glu His His His His His
                165                 170                 175

His Gly Ser Thr Thr Thr Pro Ala Pro Arg Pro Pro Thr Pro Ala Pro
            180                 185                 190

Thr Ile Ala Ser Gln Pro Leu Ser Leu Arg Pro Glu Ala Cys Arg Pro
        195                 200                 205

Ala Ala Gly Gly Ala Val His Thr Arg Gly Leu Asp Phe Ala Cys Asp
    210                 215                 220

Ile Tyr Ile Trp Ala Pro Leu Ala Gly Thr Cys Gly Val Leu Leu Leu
225                 230                 235                 240

Ser Leu Val Ile Thr Leu Tyr Cys Ser Ala Lys Arg Gly Arg Lys Lys
                245                 250                 255

Leu Leu Tyr Ile Phe Lys Gln Pro Phe Met Arg Pro Val Gln Thr Thr
            260                 265                 270

Gln Glu Glu Asp Gly Cys Ser Cys Arg Phe Pro Glu Glu Glu Glu Gly
        275                 280                 285

Gly Cys Glu Leu Arg Val Lys Phe Ser Arg Ser Ala Asp Ala Pro Ala
    290                 295                 300

Tyr Lys Gln Gly Gln Asn Gln Leu Tyr Asn Glu Leu Asn Leu Gly Arg
305                 310                 315                 320

Arg Glu Glu Tyr Asp Val Leu Asp Lys Arg Arg Gly Arg Asp Pro Glu
                325                 330                 335

Met Gly Gly Lys Pro Arg Arg Lys Asn Pro Gln Glu Gly Leu Tyr Asn
            340                 345                 350

Glu Leu Gln Lys Asp Lys Met Ala Glu Ala Tyr Ser Glu Ile Gly Met
        355                 360                 365

Lys Gly Glu Arg Arg Arg Gly Lys Gly His Asp Gly Leu Tyr Gln Gly
    370                 375                 380
```

```
Leu Ser Thr Ala Thr Lys Asp Thr Tyr Asp Ala Leu His Met Gln Ala
385                 390                 395                 400

Leu Pro Pro Arg

<210> SEQ ID NO 83
<211> LENGTH: 1232
<212> TYPE: PRT
<213> ORGANISM: Artificial Sequence
<220> FEATURE:
<223> OTHER INFORMATION: sortase immune receptor

<400> SEQUENCE: 83

Cys Thr Ala Gly Cys Thr Cys Thr Ala Gly Ala Gly Cys Cys Ala Cys
1               5                   10                  15

Cys Ala Thr Gly Gly Cys Thr Cys Thr Gly Cys Cys Thr Gly Thr Gly
                20                  25                  30

Ala Cys Ala Gly Cys Thr Cys Thr Gly Cys Thr Gly Cys Thr Gly Cys
                35                  40                  45

Cys Thr Cys Thr Gly Gly Cys Thr Cys Thr Gly Cys Thr Thr Cys Thr
            50                  55                  60

Gly Cys Ala Thr Gly Cys Cys Gly Cys Thr Ala Gly Ala Cys Cys Cys
65                  70                  75                  80

Ala Thr Gly Cys Ala Gly Gly Cys Cys Ala Ala Gly Cys Cys Thr Cys
                85                  90                  95

Ala Gly Ala Thr Cys Cys Cys Ala Ala Gly Gly Ala Cys Ala Ala Ala
                100                 105                 110

Gly Thr Cys Thr Ala Ala Gly Gly Thr Gly Gly Cys Cys Gly Gly Cys
                115                 120                 125

Thr Ala Cys Ala Thr Cys Gly Ala Gly Ala Thr Cys Cys Cys Cys Gly
            130                 135                 140

Ala Cys Gly Cys Cys Gly Ala Cys Ala Thr Cys Ala Ala Ala Gly Ala
145                 150                 155                 160

Ala Cys Cys Thr Gly Thr Gly Thr Ala Cys Cys Thr Gly Gly Ala
                165                 170                 175

Cys Cys Thr Gly Cys Cys Ala Cys Ala Gly Ala Gly Ala Gly Cys
                180                 185                 190

Ala Gly Cys Thr Gly Ala Ala Thr Ala Gly Ala Gly Gly Cys Gly Thr
                195                 200                 205

Gly Thr Cys Cys Thr Thr Cys Gly Cys Ala Ala Ala Gly Ala Gly
            210                 215                 220

Ala Ala Cys Cys Ala Gly Ala Gly Cys Cys Thr Gly Gly Ala Cys Gly
225                 230                 235                 240

Ala Cys Cys Ala Gly Ala Ala Cys Ala Thr Cys Thr Cys Thr Ala Thr
                245                 250                 255

Cys Gly Cys Cys Gly Gly Cys Cys Ala Cys Ala Cys Thr Thr Cys
                260                 265                 270

Ala Thr Cys Gly Ala Cys Ala Gly Ala Cys Cys Cys Ala Ala Cys Thr
                275                 280                 285

Ala Cys Cys Ala Gly Thr Thr Cys Ala Cys Ala Ala Cys Cys Thr
            290                 295                 300

Gly Ala Ala Gly Gly Cys Cys Gly Cys Cys Ala Ala Gly Ala Ala
305                 310                 315                 320

Gly Gly Cys Ala Gly Cys Ala Thr Gly Gly Thr Gly Thr Ala Cys Thr
                325                 330                 335
```

-continued

```
Thr Cys Ala Ala Ala Gly Thr Gly Gly Cys Ala Ala Gly Ala
            340                 345                 350
Gly Ala Cys Ala Cys Gly Ala Ala Gly Thr Ala Cys Ala Ala Gly
        355                 360                 365
Ala Thr Gly Ala Cys Cys Ala Gly Cys Ala Thr Cys Cys Gly Gly Ala
    370                 375                 380
Ala Cys Gly Thr Gly Ala Ala Gly Cys Cys Ala Cys Cys Gly Cys
385                 390                 395                 400
Thr Gly Thr Gly Gly Ala Ala Gly Thr Gly Cys Thr Gly Gly Ala Thr
                405                 410                 415
Gly Ala Gly Cys Ala Gly Ala Ala Gly Gly Cys Ala Ala Ala Gly
        420                 425                 430
Ala Cys Ala Ala Gly Cys Ala Gly Cys Thr Gly Ala Cys Cys Cys Thr
                435                 440                 445
Gly Ala Thr Cys Ala Cys Cys Thr Gly Thr Gly Ala Cys Gly Ala Cys
        450                 455                 460
Thr Ala Cys Ala Ala Cys Gly Ala Ala Gly Ala Gly Cys Ala Gly
465                 470                 475                 480
Gly Cys Gly Thr Gly Thr Gly Gly Ala Gly Ala Cys Ala Ala Gly
                485                 490                 495
Ala Ala Ala Gly Ala Thr Cys Thr Thr Cys Gly Thr Gly Gly Cys Thr
        500                 505                 510
Ala Cys Cys Gly Ala Ala Gly Thr Gly Ala Ala Gly Cys Thr Gly Gly
                515                 520                 525
Ala Ala Cys Ala Cys Cys Ala Cys Cys Ala Thr Cys Ala
530                 535                 540
Cys Cys Ala Cys Gly Gly Ala Thr Cys Ala Cys Cys Ala Cys Gly
545                 550                 555                 560
Ala Cys Gly Cys Cys Ala Gly Cys Gly Cys Gly Cys Gly Ala Cys
                565                 570                 575
Cys Ala Cys Cys Ala Ala Cys Ala Cys Cys Gly Gly Cys Gly Cys Cys
        580                 585                 590
Cys Ala Cys Cys Ala Thr Cys Gly Cys Gly Thr Cys Gly Cys Ala Gly
        595                 600                 605
Cys Cys Cys Cys Thr Gly Thr Cys Cys Cys Thr Gly Cys Gly Cys Cys
        610                 615                 620
Cys Ala Gly Ala Gly Gly Cys Gly Thr Gly Cys Gly Gly Cys Gly Cys
625                 630                 635                 640
Ala Gly Cys Gly Gly Cys Gly Gly Gly Gly Cys Gly Cys Ala
                645                 650                 655
Gly Thr Gly Cys Ala Cys Ala Cys Gly Ala Gly Gly Gly Gly Cys
            660                 665                 670
Thr Gly Gly Ala Cys Thr Thr Cys Gly Cys Cys Thr Gly Thr Gly Ala
        675                 680                 685
Thr Ala Thr Cys Thr Ala Cys Ala Thr Cys Thr Gly Gly Gly Cys Gly
                690                 695                 700
Cys Cys Cys Thr Thr Gly Gly Cys Cys Gly Gly Gly Ala Cys Thr Thr
705                 710                 715                 720
Gly Thr Gly Gly Gly Gly Thr Cys Cys Thr Cys Thr Cys Thr Cys Thr
                725                 730                 735
Gly Thr Cys Ala Cys Thr Gly Gly Thr Thr Ala Thr Cys Ala Cys Cys
            740                 745                 750
Cys Thr Thr Thr Ala Cys Thr Gly Cys Ala Gly Cys Gly Cys Thr Ala
```

-continued

```
        755                 760                 765

Ala Ala Cys Gly Gly Gly Gly Cys Ala Gly Ala Ala Ala Gly Ala Ala
    770                 775                 780

Ala Cys Thr Cys Cys Thr Gly Thr Ala Thr Ala Thr Ala Thr Thr Cys
785                 790                 795                 800

Ala Ala Ala Cys Ala Ala Cys Cys Ala Thr Thr Thr Ala Thr Gly Ala
                805                 810                 815

Gly Ala Cys Cys Ala Gly Thr Ala Cys Ala Ala Ala Cys Thr Ala Cys
            820                 825                 830

Thr Cys Ala Ala Gly Ala Gly Gly Ala Ala Gly Ala Thr Gly Gly Cys
        835                 840                 845

Thr Gly Thr Ala Gly Cys Thr Gly Cys Cys Gly Ala Thr Thr Thr Cys
    850                 855                 860

Cys Ala Gly Ala Ala Gly Ala Ala Gly Ala Ala Gly Ala Ala Gly Gly
865                 870                 875                 880

Ala Gly Gly Ala Thr Gly Thr Gly Ala Ala Cys Thr Gly Ala Gly Ala
                885                 890                 895

Gly Thr Gly Ala Ala Gly Thr Thr Cys Ala Gly Cys Ala Gly Gly Ala
            900                 905                 910

Gly Cys Gly Cys Ala Gly Ala Cys Gly Cys Cys Cys Cys Cys Gly Cys
        915                 920                 925

Gly Thr Ala Cys Ala Ala Gly Cys Ala Gly Gly Gly Cys Cys Ala Gly
    930                 935                 940

Ala Ala Cys Cys Ala Gly Cys Thr Cys Thr Ala Thr Ala Ala Cys Gly
945                 950                 955                 960

Ala Gly Cys Thr Cys Ala Ala Thr Cys Thr Ala Gly Gly Ala Cys Gly
                965                 970                 975

Ala Ala Gly Ala Gly Ala Gly Gly Ala Gly Thr Ala Cys Gly Ala Thr
            980                 985                 990

Gly Thr Thr Thr Thr Gly Gly Ala  Cys Ala Ala Gly Ala  Gly Ala Cys
        995                 1000                 1005

Gly Thr  Gly Gly Cys Cys Gly  Gly Gly Ala Cys Cys  Cys Thr Gly
    1010                 1015                 1020

Ala Gly  Ala Thr Gly Gly Gly  Gly Gly Gly Ala Ala  Ala Gly Cys
    1025                 1030                 1035

Cys Gly  Ala Gly Ala Ala Gly  Gly Ala Ala Gly Ala  Ala Cys Cys
    1040                 1045                 1050

Cys Thr  Cys Ala Gly Gly Ala  Ala Gly Gly Cys Cys  Thr Gly Thr
    1055                 1060                 1065

Ala Cys  Ala Ala Thr Gly Ala  Ala Cys Thr Gly Cys  Ala Gly Ala
    1070                 1075                 1080

Ala Ala  Gly Ala Thr Ala Ala  Gly Ala Thr Gly Gly  Cys Gly Gly
    1085                 1090                 1095

Ala Gly  Gly Cys Cys Thr Ala  Cys Ala Gly Thr Gly  Ala Gly Ala
    1100                 1105                 1110

Thr Thr  Gly Gly Gly Ala Thr  Gly Ala Ala Ala Gly  Gly Cys Gly
    1115                 1120                 1125

Ala Gly  Cys Gly Cys Cys Gly  Gly Ala Gly Gly Gly  Gly Cys Ala
    1130                 1135                 1140

Ala Gly  Gly Gly Gly Cys Ala  Cys Gly Ala Thr Gly  Gly Cys Cys
    1145                 1150                 1155

Thr Thr  Thr Ala Cys Cys Ala  Gly Gly Gly Thr Cys  Thr Cys Ala
    1160                 1165                 1170
```

```
Gly Thr Ala Cys Ala Gly Cys  Cys Ala Cys Ala  Ala Gly Gly
    1175            1180              1185

Ala Cys Ala Cys Cys Thr Ala  Cys Gly Ala Cys  Gly Cys Cys Cys
    1190            1195              1200

Thr Thr Cys Ala Cys Ala Thr  Gly Cys Ala Gly  Gly Cys Cys Cys
    1205            1210              1215

Thr Gly Cys Cys Cys Cys Cys  Thr Cys Gly Cys  Thr Ala Ala
    1220            1225              1230

<210> SEQ ID NO 84
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(5)
<223> OTHER INFORMATION: repeat n times, wherein n is an integer of at
      least 1

<400> SEQUENCE: 84

Gly Ser Gly Gly Ser
1               5

<210> SEQ ID NO 85
<211> LENGTH: 4
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(4)
<223> OTHER INFORMATION: repeat n times, wherein n is an integer of at
      least 1

<400> SEQUENCE: 85

Gly Gly Gly Ser
1

<210> SEQ ID NO 86
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(5)
<223> OTHER INFORMATION: repeat n times, wherein n is an integer of at
      least 1

<400> SEQUENCE: 86

Gly Gly Gly Gly Ser
1               5

<210> SEQ ID NO 87
<211> LENGTH: 4
<212> TYPE: PRT
<213> ORGANISM: Artificial Sequence
<220> FEATURE:
<223> OTHER INFORMATION: linker

<400> SEQUENCE: 87

Gly Gly Ser Gly
1
```

```
<210> SEQ ID NO 88
<211> LENGTH: 5
<212> TYPE: PRT
<213> ORGANISM: Artificial Sequence
<220> FEATURE:
<223> OTHER INFORMATION: linker

<400> SEQUENCE: 88

Gly Gly Ser Gly Gly
1               5

<210> SEQ ID NO 89
<211> LENGTH: 5
<212> TYPE: PRT
<213> ORGANISM: Artificial Sequence
<220> FEATURE:
<223> OTHER INFORMATION: linker

<400> SEQUENCE: 89

Gly Ser Gly Ser Gly
1               5

<210> SEQ ID NO 90
<211> LENGTH: 5
<212> TYPE: PRT
<213> ORGANISM: Artificial Sequence
<220> FEATURE:
<223> OTHER INFORMATION: linker

<400> SEQUENCE: 90

Gly Ser Gly Gly Gly
1               5

<210> SEQ ID NO 91
<211> LENGTH: 5
<212> TYPE: PRT
<213> ORGANISM: Artificial Sequence
<220> FEATURE:
<223> OTHER INFORMATION: linker

<400> SEQUENCE: 91

Gly Gly Gly Ser Gly
1               5

<210> SEQ ID NO 92
<211> LENGTH: 5
<212> TYPE: PRT
<213> ORGANISM: Artificial Sequence
<220> FEATURE:
<223> OTHER INFORMATION: linker

<400> SEQUENCE: 92

Gly Ser Ser Ser Gly
1               5

<210> SEQ ID NO 93
<211> LENGTH: 5
<212> TYPE: PRT
<213> ORGANISM: Artificial Sequence
<220> FEATURE:
<223> OTHER INFORMATION: linker

<400> SEQUENCE: 93

Gly Gly Gly Gly Ser
1               5
```

<210> SEQ ID NO 94
<211> LENGTH: 15
<212> TYPE: PRT
<213> ORGANISM: Artificial Sequence
<220> FEATURE:
<223> OTHER INFORMATION: linker

<400> SEQUENCE: 94

Gly Gly Gly Gly Ser Gly Gly Gly Gly Ser Gly Gly Gly Gly Ser
1               5                   10                  15

<210> SEQ ID NO 95
<211> LENGTH: 5
<212> TYPE: PRT
<213> ORGANISM: Artificial Sequence
<220> FEATURE:
<223> OTHER INFORMATION: hinge
<220> FEATURE:
<221> NAME/KEY: REPEAT
<222> LOCATION: (1)..(5)
<223> OTHER INFORMATION: repeat n times, wherein n is an integer of at
      least 1

<400> SEQUENCE: 95

Gly Ser Gly Gly Ser
1               5

<210> SEQ ID NO 96
<211> LENGTH: 45
<212> TYPE: DNA
<213> ORGANISM: Artificial Sequence
<220> FEATURE:
<223> OTHER INFORMATION: linker

<400> SEQUENCE: 96
ggtggcggtg gctcgggcgg tggtgggtcg ggtggcggcg gatct            45

<210> SEQ ID NO 97
<211> LENGTH: 798
<212> TYPE: DNA
<213> ORGANISM: Artificial Sequence
<220> FEATURE:
<223> OTHER INFORMATION: Her2 scFv

<400> SEQUENCE: 97
atggattttc aggtgcagat tttcagcttc ctgctaatca gtgcctcagt cataatgtcc      60
agaggagata tccagatgac ccagtccccg agctccctgt ccgcctctgt gggcgatagg     120
gtcaccatca cctgccgtgc cagtcaggat gtgaatactg ctgtagcctg gtatcaacag     180
aaaccaggaa aagctccgaa actactgatt tactcggcat ccttccttta ttctggagtc     240
ccttctcgct tctctggatc tagatctggg acggatttca ctctgaccat cagcagtctg     300
cagccggaag acttcgcaac ttattactgt cagcaacatt atactactcc tcccacgttc     360
ggacagggta ccaaggtgga gatcaaacgc actgggtcta catctggatc tgggaagccg     420
ggttctggtg agggttctga ggttcagctg gtggagtctg gcggtggcct ggtgcagcca     480
gggggctcac tccgtttgtc ctgtgcagct tctggcttca acattaaaga cacctatata     540
cactgggtgc gtcaggcccc gggtaagggc ctggaatggg ttgcaaggat ttatcctacg     600
aatggttata ctagatatgc cgatagcgtc aagggccgtt tcactataag cgcagacaca     660
tccaaaaaca cagcctacct gcagatgaac agcctgcgtg ctgaggacac tgccgtctat     720
tattgttcta gatggggagg ggacggcttc tatgctatgg acgtgtgggg tcaaggaacc     780
ctggtcaccg tctcctcg    798

<210> SEQ ID NO 98
<211> LENGTH: 266
<212> TYPE: PRT
<213> ORGANISM: Artificial Sequence
<220> FEATURE:
<223> OTHER INFORMATION: Her2 scFv

<400> SEQUENCE: 98

```
Met Asp Phe Gln Val Gln Ile Phe Ser Phe Leu Leu Ile Ser Ala Ser
1               5                   10                  15

Val Ile Met Ser Arg Gly Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Lys Pro Gly Lys
    50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
        115                 120                 125

Lys Arg Thr Gly Ser Thr Ser Gly Ser Gly Lys Pro Gly Ser Gly Glu
    130                 135                 140

Gly Ser Glu Val Gln Leu Val Glu Ser Gly Gly Gly Leu Val Gln Pro
145                 150                 155                 160

Gly Gly Ser Leu Arg Leu Ser Cys Ala Ala Ser Gly Phe Asn Ile Lys
                165                 170                 175

Asp Thr Tyr Ile His Trp Val Arg Gln Ala Pro Gly Lys Gly Leu Glu
            180                 185                 190

Trp Val Ala Arg Ile Tyr Pro Thr Asn Gly Tyr Thr Arg Tyr Ala Asp
        195                 200                 205

Ser Val Lys Gly Arg Phe Thr Ile Ser Ala Asp Thr Ser Lys Asn Thr
    210                 215                 220

Ala Tyr Leu Gln Met Asn Ser Leu Arg Ala Glu Asp Thr Ala Val Tyr
225                 230                 235                 240

Tyr Cys Ser Arg Trp Gly Gly Asp Gly Phe Tyr Ala Met Asp Val Trp
                245                 250                 255

Gly Gln Gly Thr Leu Val Thr Val Ser Ser
            260                 265
```

<210> SEQ ID NO 99
<211> LENGTH: 1212
<212> TYPE: DNA
<213> ORGANISM: Artificial Sequence
<220> FEATURE:
<223> OTHER INFORMATION: sortase CAR

<400> SEQUENCE: 99
atggctctgc ctgtgacagc tctgctgctg cctctggctc tgcttctgca tgccgctaga    60
cccatgcagg ccaagcctca gatccccaag acaagtcta aggtggccgg ctacatcgag    120
atccccgacg ccgacatcaa agaacctgtg taccctggac ctgccaccag agagcagctg    180

```
aatagaggcg tgtccttcgc caaagagaac cagagcctgg acgaccagaa catctctatc    240
gccggccaca ccttcatcga cagacccaac taccagttca ccaacctgaa ggccgccaag    300
aaaggcagca tggtgtactt caaagtgggc aacgagacac ggaagtacaa gatgaccagc    360
atccggaacg tgaagcccac cgctgtggaa gtgctggatg agcagaaggg caaagacaag    420
cagctgaccc tgatcacctg tgacgactac aacgaagaga caggcgtgtg ggagacaaga    480
aagatcttcg tggctaccga agtgaagctg aacaccacc accatcacca cggatccacc    540
acgacgccag cgccgcgacc accaacaccg gcgcccacca tcgcgtcgca gcccctgtcc    600
ctgcgcccag aggcgtgccg gccagcgcg ggggcgcag tgcacacgag ggggctggac    660
ttcgcctgtg atatctacat ctgggcgccc ttggccggga cttgtggggt ccttctcctg    720
tcactggtta tcacccttta ctgcagcgct aaacggggca gaaagaaact cctgtatata    780
ttcaaacaac catttatgag accagtacaa actactcaag aggaagatgg ctgtagctgc    840
cgatttccag aagaagaaga aggaggatgt gaactgagag tgaagttcag caggagcgca    900 gacgccccg cgtacaagca gggccagaac cagctctata cgagctcaa tctaggacga    960 agagaggagt acgatgtttt ggacaagaga cgtggccggg accctgagat gggggaaag   1020 ccgagaagga agaaccctca ggaaggcctg tacaatgaac tgcagaaaga taagatggcg   1080
gaggcctaca gtgagattgg gatgaaaggc gagcgccgga ggggcaaggg gcacgatggc   1140
ctttaccagg gtctcagtac agccaccaag gacacctacg acgcccttca catgcaggcc   1200
ctgccccctc gc                                                       1212
```

<210> SEQ ID NO 100
<211> LENGTH: 404
<212> TYPE: PRT
<213> ORGANISM: Artificial Sequence
<220> FEATURE:
<223> OTHER INFORMATION: sortase CAR

<400> SEQUENCE: 100

```
Met Ala Leu Pro Val Thr Ala Leu Leu Leu Pro Leu Ala Leu Leu Leu
1               5                   10                  15

His Ala Ala Arg Pro Met Gln Ala Lys Pro Gln Ile Pro Lys Asp Lys
            20                  25                  30

Ser Lys Val Ala Gly Tyr Ile Glu Ile Pro Asp Ala Asp Ile Lys Glu
        35                  40                  45

Pro Val Tyr Pro Gly Pro Ala Thr Arg Glu Gln Leu Asn Arg Gly Val
    50                  55                  60

Ser Phe Ala Lys Glu Asn Gln Ser Leu Asp Asp Gln Asn Ile Ser Ile
65                  70                  75                  80

Ala Gly His Thr Phe Ile Asp Arg Pro Asn Tyr Gln Phe Thr Asn Leu
                85                  90                  95

Lys Ala Ala Lys Lys Gly Ser Met Val Tyr Phe Lys Val Gly Asn Glu
            100                 105                 110

Thr Arg Lys Tyr Lys Met Thr Ser Ile Arg Asn Val Lys Pro Thr Ala
        115                 120                 125

Val Glu Val Leu Asp Glu Gln Lys Gly Lys Asp Lys Gln Leu Thr Leu
    130                 135                 140

Ile Thr Cys Asp Asp Tyr Asn Glu Glu Thr Gly Val Trp Glu Thr Arg
145                 150                 155                 160

Lys Ile Phe Val Ala Thr Glu Val Lys Leu Glu His His His His
                165                 170                 175
```

```
His Gly Ser Thr Thr Thr Pro Ala Pro Arg Pro Thr Pro Ala Pro
            180                 185                 190

Thr Ile Ala Ser Gln Pro Leu Ser Leu Arg Pro Glu Ala Cys Arg Pro
        195                 200                 205

Ala Ala Gly Gly Ala Val His Thr Arg Gly Leu Asp Phe Ala Cys Asp
    210                 215                 220

Ile Tyr Ile Trp Ala Pro Leu Ala Gly Thr Cys Gly Val Leu Leu Leu
225                 230                 235                 240

Ser Leu Val Ile Thr Leu Tyr Cys Ser Ala Lys Arg Gly Arg Lys Lys
                245                 250                 255

Leu Leu Tyr Ile Phe Lys Gln Pro Phe Met Arg Pro Val Gln Thr Thr
            260                 265                 270

Gln Glu Glu Asp Gly Cys Ser Cys Arg Phe Pro Glu Glu Glu Glu Gly
            275                 280                 285

Gly Cys Glu Leu Arg Val Lys Phe Ser Arg Ser Ala Asp Ala Pro Ala
        290                 295                 300

Tyr Lys Gln Gly Gln Asn Gln Leu Tyr Asn Glu Leu Asn Leu Gly Arg
305                 310                 315                 320

Arg Glu Glu Tyr Asp Val Leu Asp Lys Arg Arg Gly Arg Asp Pro Glu
                325                 330                 335

Met Gly Gly Lys Pro Arg Arg Lys Asn Pro Gln Glu Gly Leu Tyr Asn
            340                 345                 350

Glu Leu Gln Lys Asp Lys Met Ala Glu Ala Tyr Ser Glu Ile Gly Met
        355                 360                 365

Lys Gly Glu Arg Arg Arg Gly Lys Gly His Asp Gly Leu Tyr Gln Gly
    370                 375                 380

Leu Ser Thr Ala Thr Lys Asp Thr Tyr Asp Ala Leu His Met Gln Ala
385                 390                 395                 400

Leu Pro Pro Arg

<210> SEQ ID NO 101
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: X
<222> LOCATION: (1)..(1)
<223> OTHER INFORMATION: Xaa is L or N
<220> FEATURE:
<221> NAME/KEY: X
<222> LOCATION: (2)..(2)
<223> OTHER INFORMATION: Xaa is P or A
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: X
<222> LOCATION: (5)..(5)
<223> OTHER INFORMATION: Xaa is G or A

<400> SEQUENCE: 101

Xaa Xaa Xaa Thr Xaa
1               5

<210> SEQ ID NO 102
<211> LENGTH: 5
<212> TYPE: PRT
<213> ORGANISM: Artificial Sequence
<220> FEATURE:
```

<223> OTHER INFORMATION: sortase recognition motif
<220> FEATURE:
<221> NAME/KEY: X
<222> LOCATION: (3)..(3)
<223> OTHER INFORMATION: Xaa is E, A, S, or H

<400> SEQUENCE: 102

Asn Ala Xaa Thr Gly
1               5

<210> SEQ ID NO 103
<211> LENGTH: 450
<212> TYPE: DNA
<213> ORGANISM: Artificial Sequence
<220> FEATURE:
<223> OTHER INFORMATION: Sortase

<400> SEQUENCE: 103

```
atgcaggcca agcctcagat ccccaaggac aagtctaagg tggccggcta catcgagatc     60
cccgacgccg acatcaaaga acctgtgtac cctggacctg ccaccagaga gcagctgaat    120
agaggcgtgt ccttcgccaa agagaaccag agcctggacg accagaacat ctctatcgcc    180
ggccacacct tcatcgacag acccaactac cagttcacca acctgaaggc cgccaagaaa    240
ggcagcatgg tgtacttcaa agtgggcaac gagacacgga agtacaagat gaccagcatc    300
cggaacgtga agcccaccgc tgtggaagtg ctggatgagc agaagggcaa agacaagcag    360
ctgaccctga tcacctgtga cgactacaac gaagagacag gcgtgtggga caagaaaag    420 atcttcgtgg ctaccgaagt gaagctggaa                                    450
```

<210> SEQ ID NO 104
<211> LENGTH: 63
<212> TYPE: DNA
<213> ORGANISM: Artificial Sequence
<220> FEATURE:
<223> OTHER INFORMATION: Signal sequence

<400> SEQUENCE: 104

```
atggctctgc ctgtgacagc tctgctgctg cctctggctc tgcttctgca tgccgctaga     60
ccc                                                                   63
```

<210> SEQ ID NO 105
<211> LENGTH: 135
<212> TYPE: DNA
<213> ORGANISM: Artificial Sequence
<220> FEATURE:
<223> OTHER INFORMATION: CD8 hinge

<400> SEQUENCE: 105

```
accacgacgc cagcgccgcg accaccaaca ccggcgccca ccatcgcgtc gcagcccctg     60
tccctgcgcc cagaggcgtg ccggccagcg gcggggggcg cagtgcacac gagggggctg    120
gacttcgcct gtgat                                                    135
```

<210> SEQ ID NO 106
<211> LENGTH: 72
<212> TYPE: DNA
<213> ORGANISM: Artificial Sequence
<220> FEATURE:
<223> OTHER INFORMATION: CD8 transmembrane domain

<400> SEQUENCE: 106

```
atctacatct gggcgcccct tggccgggact tgtggggtcc ttctcctgtc actggttatc     60
```

```
acccttttact gc                                                        72

<210> SEQ ID NO 107
<211> LENGTH: 126
<212> TYPE: DNA
<213> ORGANISM: Artificial Sequence
<220> FEATURE:
<223> OTHER INFORMATION: 4-1BB

<400> SEQUENCE: 107
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 108
<211> LENGTH: 336
<212> TYPE: DNA
<213> ORGANISM: Artificial Sequence
<220> FEATURE:
<223> OTHER INFORMATION: CD3 zeta

<400> SEQUENCE: 108
agagtgaagt tcagcaggag cgcagacgcc cccgcgtaca gcagggcca gaaccagctc     60 tataacgagc tcaatctagg acgaagagag gagtacgatg ttttggacaa gagacgtggc   120
cgggaccctg agatggggg aaagccgaga aggaagaacc ctcaggaagg cctgtacaat    180
gaactgcaga agataagat ggcggaggcc tacagtgaga ttgggatgaa aggcgagcgc    240
cggaggggca gggggcacga tggcctttac cagggtctca gtacagccac caaggacacc    300
tacgacgccc ttcacatgca ggccctgccc cctcgc                             336

<210> SEQ ID NO 109
<211> LENGTH: 21
<212> TYPE: PRT
<213> ORGANISM: Artificial Sequence
<220> FEATURE:
<223> OTHER INFORMATION: Signal sequence

<400> SEQUENCE: 109

Met Ala Leu Pro Val Thr Ala Leu Leu Leu Pro Leu Ala Leu Leu Leu
1               5                   10                  15

His Ala Ala Arg Pro
            20

<210> SEQ ID NO 110
<211> LENGTH: 150
<212> TYPE: PRT
<213> ORGANISM: Artificial Sequence
<220> FEATURE:
<223> OTHER INFORMATION: Sortase

<400> SEQUENCE: 110

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
                20                  25                  30

Pro Ala Thr Arg Glu Gln Leu Asn Arg Gly Val Ser Phe Ala Lys Glu
            35                  40                  45

Asn Gln Ser Leu Asp Asp Gln Asn Ile Ser Ile Ala Gly His Thr Phe
        50                  55                  60

Ile Asp Arg Pro Asn Tyr Gln Phe Thr Asn Leu Lys Ala Ala Lys Lys
```

```
                65                  70                  75                  80
Gly Ser Met Val Tyr Phe Lys Val Gly Asn Glu Thr Arg Lys Tyr Lys
                    85                  90                  95

Met Thr Ser Ile Arg Asn Val Lys Pro Thr Ala Val Glu Val Leu Asp
                    100                 105                 110

Glu Gln Lys Gly Lys Asp Lys Gln Leu Thr Leu Ile Thr Cys Asp Asp
                    115                 120                 125

Tyr Asn Glu Glu Thr Gly Val Trp Glu Thr Arg Lys Ile Phe Val Ala
    130                 135                 140

Thr Glu Val Lys Leu Glu
145                 150

<210> SEQ ID NO 111
<211> LENGTH: 45
<212> TYPE: PRT
<213> ORGANISM: Artificial Sequence
<220> FEATURE:
<223> OTHER INFORMATION: CD8 hinge

<400> SEQUENCE: 111

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 112
<211> LENGTH: 24
<212> TYPE: PRT
<213> ORGANISM: Artificial Sequence
<220> FEATURE:
<223> OTHER INFORMATION: CD8 transmembrane

<400> SEQUENCE: 112

Ile Tyr Ile Trp Ala Pro Leu Ala Gly Thr Cys Gly Val Leu Leu Leu
1               5                   10                  15

Ser Leu Val Ile Thr Leu Tyr Cys
                20

<210> SEQ ID NO 113
<211> LENGTH: 42
<212> TYPE: PRT
<213> ORGANISM: Artificial Sequence
<220> FEATURE:
<223> OTHER INFORMATION: 4-1BB

<400> SEQUENCE: 113

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 114
<211> LENGTH: 112
<212> TYPE: PRT
<213> ORGANISM: Artificial Sequence
<220> FEATURE:
<223> OTHER INFORMATION: CD3 zeta
```

```
<400> SEQUENCE: 114

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110
```